United States Patent [19]

Desnick et al.

[11] Patent Number: 5,840,578
[45] Date of Patent: Nov. 24, 1998

[54] METHODS FOR DETERMINING SUSCEPTIBILITY TO LEAD POISONING

[75] Inventors: Robert J. Desnick, New York; James G. Wetmur, Scarsdale, both of N.Y.

[73] Assignee: Mount Sinai School of Medicine of the City University of New York, New York, N.Y.

[21] Appl. No.: 788,279

[22] Filed: Jan. 24, 1997

Related U.S. Application Data

[62] Division of Ser. No. 195,744, Feb. 14, 1994, Pat. No. 5,639,607, which is a continuation of Ser. No. 742,130, Aug. 7, 1991, abandoned.

[51] Int. Cl.$^6$ ............................... C12N 5/00; C12N 15/00
[52] U.S. Cl. ........................ 435/325; 435/320.1; 435/348; 435/252.3; 435/255.1; 536/23.5; 935/22; 935/69; 935/70; 935/72
[58] Field of Search ............................... 800/2; 536/23.1, 536/23.5; 435/320.1, 325, 348, 252.3, 255.1; 935/22, 89, 70, 72

[56] References Cited

U.S. PATENT DOCUMENTS 4,683,195  7/1987  Mullis et al. ............................... 435/91

OTHER PUBLICATIONS

Wetmur J.G., et al., "Molecular Characteristization of the Human δ–Aminolevulinate Dehydratase 2 (ALAD$^2$) Allele: Implications for Molecular Screening of Individuals for Genetic Susceptibility to Lead Poisoning", Am.J.Hum.Genet. (1991), 49:757.

Wong et al., "Branch Capture Reactions: Displacers Derived From Asymmetric PCR", Nucleic Acids Res., (1991) 19:9, p. 2251.

Bishop T.R., et al., "Nucleotide Sequence of Rat Liver δ–aminolevulinic Dehydratase cDNA", Nucleic Acids Res., (1986), 14, 24:10115.

Bishop T.R., et al., "Cloning and Sequence of Mouse erythroid δ–aminolevulinate Dehydratase cDNA", Nucleic Acids Res., (1989), 17, 4:1775.

Chisolm J.J. Jr. et al., "Erythrocyte Porphobilinogen Synthase Activity as an Indicator of Lead Exposure in Children", Clin. Chem., (1985), 31, 4:601.

Claudio L., et al., "Increased Vesicular Transport and Decreased Mitochondrial Content in Blood–Brain Barrier Endothelial Cells During Experimental Autoimmune Encephalomyelitis", Amer.J.Path., (1989), 135, 6:1157.

Jaffe E.K., et al., "Reevaluation of a Sensitive Indicator of Early Lead Exposure", Biol.Trace Element Res., (1991), 28:223.

Seppalainen et al., "Early Neurotoxic Effects of Occupational Lead Exposure: A Prospective Study", NeuroToxicology, (1983), 4:181.

Needleman et al., "Deficits in Psychologic and Classroom Performance of Children With Elevated Dentine Lead Levels", N.Engl.J.Med., (1979), 300:689.

Baker et al., "Occupational Lead Neurotoxicity: Improvement in Behavioural Effects After Reduction of Exposure", Brit.J.Industr.Med., (1985), 42:507.

Jeyaratnam et al., "Neuropsychological Studies on Lead Workers in Singapore", Brit.J.Industr.Med., (1986), 43:626.

Lilis et al., "Effects of Low–Level Lead and Arsenic Exposure on Copper Smelter Workers", Arch.Env.Health, (1985), 40:38.

Winneke et al., "Neuropsychological Comparison of Children With Different Tooth–Lead Levels. Preliminary Report", Internat.Conf. on Heavy Metals in the Environment, Geneva, World Health Organization, (1981), pp. 553–556.

Smith et al., "The Effects of Lead Exposure on Urban Children: The Institute of Child Health/Southampton Study", Dev.Med.Child.Neurol., (1983), 47:1.

Bellinger et al., "Longitudinal Analyses of Prenatal and Postnatal Lead Exposure and Early Cognitive Development", N.Engl.J.Med., (1987), 316:1037.

Gerber et al., "Toxicity, Mutagenicity and Teratogenicity of Lead", Muta.Res., (1980), 76:115.

Wibberley et al., "Lead Levels in Human Placentae from Normal and Malformed Births", J.Med.Genet., (1977), 14:339.

Needleman et al., "The Relationship Between Prenatal Exposure to Lead and Congenital Anomalies", J.Amer.Med.Assoc., (1984), 251:2956.

Deknudt et al., "Chromosome Aberrations Observed in Male Workers Occupationally Exposed to Lead", Environ.Physiol.Biochem., (1973), 3:132.

Wu et al., "The Quaternary Structure of δ–Aminolevulinic Acid Dehydratase from Bovine Liver", Proc.Natl.Acad.Sci. USA, (1974), 71:1767.

Gurne et al., "Dissociation and Reassociation of Immobilized Porphobilinogen Synthase: Use of Immobilized Subunits for Enzyme Isolation", Proc.Natl.Acad.Sci. USA, (1977), 74:1383.

Anderson and Desnick, "Purification and Properties of δ–Aminolevulinate Dehydrase from Human Erythrocytes", J.Biol.Chem., (1979), 254:6924.

Bevan et al., "Mechanism of Porphobilinogen Synthase", J.Biol.Chem., (1980), 255:2030.

Tsukamoto et al., "The Role of Zinc With Special Reference to the Essential Thiol Groups in δ–aminolevulinic Acid Dehydratase of Bovine Liver", Biochem.Biophys.Acta, (1979), 570:167.

Tsukamoto et al., "Zinc and Cysteine Residues in the Active Site of Bovine Liver δ–aminolevulinic Acid Dehydratase", Int.J.Biochem., (1980), 12:751.

(List continued on next page.)

*Primary Examiner*—Bruce R. Campell
*Attorney, Agent, or Firm*—Baker & Botts, LLP

[57] ABSTRACT

A DNA sequence encoding the δ-amino levulinate type 2 gene, methods to detect the gene, diagnostic kits to detect the gene and recombinant vectors containing the type 2 gene sequence.

9 Claims, 1 Drawing Sheet

OTHER PUBLICATIONS

Jaffe et al., "Porphobilinogen Synthase Modification with Methylmethanethiosulfonate", J.Biol.Chem., (1984), 259:5032.

Jordan et al., "Mechanism of Action of 5–aminolaevulinate Deshydratase from Human Erythrocytes", Biochem.J., 227:1015.

Morgan and Burch, "Comparative Tests for Diagnosis of Lead Poisoning", Arch.Intern.Med., (1972), 130:335.

Chisholm et al., "Chronic Lead Intoxication in Children", Dev.Med.Child.Neurol., (1965), 7:529.

Petrucci et al., "The Genetic Polymorphism of Delta–aminolaevulinate Deshydrase in Italy", Hum.Genet., (1982), 60:289.

Battistuzzi et al., "δ–aminolaevulinate Deshydrase: A New Genetic Polymorphism in Man", Ann.Hum.Genet., (1981), 45:223.

Potluri et al., "Human δ–aminolaevulinate Deshydratase: Chromosomal Localization to 9q34 by In Situ Hybridization", Hum.Genet., (1987), 76:236.

Benkmann et al., Polymorphism of Delta–Aminolevulinic Acid Dehydratase in Various Populations, Hum.Hered., (1983), 33:62.

Propping, "Pharmacogenetics", J.Physiol.Biochem.Pharmacol., (1978), 83:124.

Ziemsen et al., "Polymorphism of Delta–aminolevulinic Acid Dehydratase in Lead–Exposed Workers", Int.Arch.Occup.Environ.Health, (1986), 58:245.

Ben–Ezzer et al., "Genetic Polymorphism of Delta–Aminolevulinate Dehydrase In Several Population Groups in Israel", Hum.Hered., (1987), 37:229.

Connor et al., "Detection of Sickle Cell $\beta^s$–Globin Allele by Hybridization with Synthetic Oligonucleotides", Proc.Natl.Acad.Sci. USA, (1983), 80:278.

Saiki et al., "Analysis of Enzymatically Amplified β–Globin and HLA–$DQ_\alpha$ DNA with Allele–Specific Oligonucleotide Probes", Nature, (1986), 324:163.

Chehab et al., "Detection of Sickle Cell Anaemia and Thalassaemias", Nature, (1987), 329:293.

Landegren et al., "A Ligase–Mediated Gene Detection Technique", Science, (1988), 241:1077.

Wu et al., "Allele–Specific Enzymatic Amplification of β–Globin Genomic DNA for Diagnosis of Sickle Cell Anemia", (1989), Proc.Natl.Acad.Sci.USA, (1989), 86:2757.

Wu et Wallace, "The Ligation Amplification Reaction (LAR)—Amplifaction of Specific DNA Sequences Using Sequential Rounds of Template–Dependent Ligation", Genomics, (1989), 4:560.

Gordon and Ruddle, "Gene Transfer into Mouse Embryos: Production of Transgenic Mice by Pronuclear Injection", Methods Enzymol., (1983), 101:411.

Southern, "Detection of Specific Sequences Among DNA Fragments Separated by Gel Electrophoresis", J.Mol.Biol., (1975), 98:503.

Saiki et al., "Primer–Directed Enzymatic Amplification of DNA with a Thermostable DNA Polymerase", Science (1988), 239:487.

Botstein et al., "Construction of a Genetic Linkage Map in Man Using Restriction Fragment Length Polymorphisms", Am.J.Hum.Genet., (1980), 32:314.

Pasvol et al., "Cellular Mechanism for the Protective Effect of Haemoglobin S. Against P. falciparum Malaria", Nature, (1978), 274:7801.

Astrin et al., "δ–Aminolevulinic Acid Deshydratase Isozymes and Lead Toxicity", Ann.N.Y.Acad.Sci., (1987), 514:23.

Wetmur et al., "Human δ–aminolevulinate Deshydratase: Nucleotide Sequence of a Full–length cDNA Clone", Proc. Natl.Acad.Sci. USA, (1986), 83:7703.

Chirgwin et al., "Isolation of Biologically Active Ribonucleic Acid From Sources Enriched in Ribonuclease", Biochem., (1979), 18:5294.

Kushner et al., "An Improved Method for Transformation of *Escherichia coli* with ColE1 Derived Plasmids", Genetic Engineering, Boyer Nicosia, eds. Elsevier/North–Holland Biomedical Press, Amsterdam, (1978), pp. 17–23.

Wetmur J.G., et al., "The δ–aminolevulinate Dehydratase Polymorphism: Higher Blood Lead Levels in Lead Workers and Environmentally Exposed Children with the 1–2 and 2–2 Isozymes", Environ. Res., (1991), 56:109.

Wetmur et al PNAS 83:7703, 1986.

Wetmur et al Am. J. Human Genetics 49:757, 1991.

Palmuter et al Am. Rev. Genet. 20:465, 1986.

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 20 BASES
        ( B ) TYPE: NUCLEIC ACID
        ( C ) STRANDEDNESS: SINGLE
        ( D ) TOPOLOGY: LINEAR ( i i ) MOLECULE TYPE:
        ( A ) DESCRIPTION: OTHER NUCLEIC ACID, SYNTHETIC ( i i i ) HYPOTHETICAL: NO ( i v ) ANTI-SENSE: NO ( v i i ) IMMEDIATE SOURCE:
        ( A ) LIBRARY: SYNTHETIC ( x ) PUBLICATION INFORMATION: NONE ( x i ) SEQUENCE DESCRIPTION: SEQ ID NO:1:

AGACAGACATT AGCTCAGTA                                                                                    20

( 2 ) INFORMATION FOR SEQ ID NO: 2:

( i ) SEQUENCE CHARACTERISTICS:
        ( A ) LENGTH: 20 BASES
        ( B ) TYPE: NUCLEIC ACID
        ( C ) STRANDEDNESS: SINGLE
        ( D ) TOPOLOGY: LINEAR ( i i ) MOLECULE TYPE:
        ( A ) DESCRIPTION: OTHER NUCLEIC ACID/SYNTHETIC ( i i i ) HYPOTHETICAL: NO ( i v ) ANTI-SENSE: NO ( v i i ) IMMEDIATE SOURCE:
        ( A ) LIBRARY: SYNTHETIC ( x ) PUBLICATION INFORMATION: NONE ( x i ) SEQUENCE DESCRIPTION: SEQ ID NO: 2:

GGCAAAGACC ACGTCCATTC                                                                                    20

( 2 ) INFORMATION FOR SEQ ID NO: 3:

( i ) SEQUENCE CHARACTERISTICS:
        ( A ) LENGTH: 1222 BASE PAIRS
        ( B ) TYPE: NUCLEIC ACID ( C ) STRANDEDNESS: DOUBLE
( D ) TOPOLOGY: LINEAR ( i i ) MOLECULE TYPE:
( A ) DESCRIPTION: cDNA TO mRNA ( i i i ) HYPOTHETICAL: NO ( i v ) ANTI-SENSE: NO ( v i ) ORIGINAL SOURCE:
( A ) ORGANISM: HUMAN
( F ) TISSUE TYPE: LYMPHOBLASTOID CELLS ( v i i ) IMMEDIATE SOURCE:
( A ) LIBRARY: cDNA ( i x ) FEATURE:
( D ) OTHER INFORMATION: GENE PRODUCT IS k-AMINO LEVULINATE DEHYDRATASE ( x ) PUBLICATION INFORMATION: NONE ( x i ) SEQUENCE DESCRIPTION: SEQ ID NO: 3:

```
GAGACCGGAG CGGGAGACAG CGGTGACAGG AGCAGCGGCC GGGAGCCCTT            50

AGGGAGGCAG ACAGAGCCTG CAGCCAATGC CCCAGGAGCC CTCGGTTCCA           100

ACCAACTGAT GCCCCTGTGC CCACTGGCCC ACGCC ATG CAG CCC CAG           147

TCC GTT CTG CAC AGC GGC TAC TTC CAC CCA CTA CTT CGG GCC          189

TGG CAG ACA GCC ACC ACC ACC CTC AAT GCC TCC AAC CTC ATC          231

TAC CCC ATC TTT GTC ACG GAT GTT CCT GAT GAC ATA CAG CCT          273

ATC ACC AGC CTC CCA GGA GTG GCC AGG TAT GGT GTG AAC CGG          315

CTG GAA GAG ATG CTG AGG CCC TTG GTG AAA GAG GGC CTA CGC          357

TGT GTC TTG ATC TTT GGC GTC CCC AGC AGA GTT CCC AAG GAC          399

GAG CGG GGT TCC GCA GCT GAC TCC GAG GAG TCC CCA GCT ATT          441

GAG GCA ATC CAT CTG TTG AGG AAG ACC TTC CCC AAC CTC CTG          483

GTG GCC TGT GAT GTC TGC CTG TGT CCC TAC ACC TCC CAT GGT          525

CAC TGC GGG CTC CTG AGT GAA AAC GGA GCA TTC CGG GCT GAG          567

GAG AGC CGC CAG CGG CTG GCT GAG GTG GCA TTG GCG TAT GCC          609

AAG GCA GGA TGT CAG GTG GTA GCC CCG TCG GAC ATG ATG GAT          651

GGA CGC GTG GAA GCC ATC AAA GAG GCC CTG ATG GCA CAT GGA          693

CTT GGC AAC AGG GTA TCG GTG ATG AGC TAC AGT GCC AAA TTT          735

GCT TCC TGT TTC TAT GGC CCT TTC CGG GAT GCA GCT AAG TCA          777

AGC CCA GCT TTT GGG GAC CGC CGC TGC TAC CAG CTG CCC CCT          819

GGA GCA CGA GGC CTG GCT CTC CGA GCT GTG GAC CGG GAT GTA          861

CGG GAA GGA GCT GAC ATG CTC ATG GTG AAG CCG GGA ATG CCC          903

TAC CTG GAC ATC GTG CGG GAG GTA AAG GAC AAG CAC CCT GAC          945

CTC CCT CTC GCC GTG TAC CAC GTC TCT GGA GAG TTT GCC ATG          987

CTG TGG CAT GGA GCC CAG GCC GGG CAT TTT GAT CTC AAG GCT         1029

GCC GTA CTG GAG GCC ATG ACT GCC TTC CGC AGA GCA GGT GCT         1071

GAC ATC ATC ATC ACC TAC TAC ACA CCG CAG CTG CTG CAG TGG         1113

CTG AAG GAG GAA TGA TGGAGACAGT GCCAGGCCCA AGAACTAGAA            1158

CTTTAAAACG TTCCCGGGGC CTCAGACAAG TGAAAACCAA AGTAAATGCT         1208
```

```
GCTTTTAGAA CTGT                                                                         1222
```

( 2 ) INFORMATION FOR SEQ ID NO: 4:

( i ) SEQUENCE CHARACTERISTICS:
       ( A ) LENGTH: 6063
       ( B ) TYPE: NUCLEIC ACID
       ( C ) STRANDEDNESS: DOUBLE
       ( D ) TOPOLOGY: LINEAR ( i i ) MOLECULE TYPE:
       ( A ) DESCRIPTION: GENOMIC DNA ( i i i ) HYPOTHETICAL: YES ( i v ) ANTI-SENSE: NO ( i x ) FEATURE:
       ( D ) OTHER INFORMATION: GENE PRODUCT IS k-AMINO LEVULINATE
             DEHYDRATASE ( x ) PUBLICATION INFORMATION: NONE ( x i ) SEQUENCE DESCRIPTION: SEQ ID NO: 4:

```
GAGACCATCC TGGGAAGCAT GGCAAGACCT CCATCTCTAC AAAAAATTCG                50
AAAATTAGCT GGATGTTGTG GTGCACACCT GCAGTCCCAG CTACTTGGGA                100
GGCTGAGTTG GGAGAAACAG TTGAGCCCGG GAGGTCAAGG CTGCAGTGAG                150
TCGAGATTGC ACCACTGCAC TCCAGCCTGG GCGACAGAGA CCCTGTGTGA                200
AAAAAAAAAA AAGAAGAGAA TTTTTTTTAA ACAGTCATTG CTTGCTCAGA                250
TGTTTACTTT AAAAGATAAT AATGAACAAG AAGCAGTCAC ATAAAATACA                300
AGCCCAAATT TTATATCATT AGATTCTGAT TGTCATGAAA GTTTCTAAAG                350
ACTTACTTTC ATTTCTCAAC TTACCTTGTT GACCAGCAGG GATTGGTGAA                400
CCAGGCTGTG AGTAGCATTG GGCTAGAGAG AGGGGAGGCA GGAATCTAGA                450
AGAGCTGTTT TCCAGATGTG ACCATCTCCT GAGGACAGGG ACCATGTCCT                500
ATGTGCCACC CATCACCCCC CACAGACAGA GCCTGCAGCC AATGCCCAG                 550
GAGCCCTCGG TTCCAACCAA CTGATGCCCC TGTGCCCACT GGCCCACGCC                600
ATG CAG CCC CAG TCC GTT CTG CAC AGC GGC TAC TTC CAC CCA               642
CTA CTT CGG GCC TGG CAG ACA GCC ACC ACC ACC CTC AAT GCC               684
TCC AAC CTC ATC TAC CCC ATC TTT GTC AC GTGAGTCTCC                     723
AAGAATGGGC CAGGCCTCTG CTCTGCTGGT TGGGGTTGGG GTTGGGGAGG                773
GAGTGTTGAC TGGAGCGGGC ATCAGTATGG CTGGGGGTGG CAAAGTGAGC                823
TGTCAGCTTG AAATTCAAGG CACTGGAAGC AGGCTACTTG GATTAAGGAC                873
AGGAATCTTA GGAACAAAAC AAACTTTGAA AGAACTCATT CATCCCATTT                923
GGAAAATTAG AAGAATAACC CTTGCCTGCC ATCCTGAGCT CTTGCAGTAA                973
GACAGAAGCT GAGAAGGTGC TCTGTACATT GTAAAGTGCT ATGTACCTGT                1023
AAGAGATGGC AGTCATTGAG GCTGGGCACG GTGGCTCACG CCTGTAATCC                1073
CAGCACTTTG GGAGGCTGAG GCAGGCGGAT CACGAGGTCA GGAGATCGAG                1123
ACCATCCTGG CTAATATGGT GAAACCCTGT CTCTACTAAA AACACAAAGA                1173
AATTAGCCAG GCGTGGTGGC GGGTGCCTGT AGTCCAGCT ACTTGGGAGG                 1223
CTGAGGCAGG AGAATGGCGT GAACCCGGGA GGCGGAGCTT GCAGTGAGCC                1273
GAGATTGCAC CACTTCACTC CAGCCTGGGC GACAGAGCCA GACTCCATCT                1323
```

```
CAAAAAAAAA AAAAAAAAA AGAGATGGCA ATCGTGATTG TTAATAATAA      1373
TGCAGACATT TACTGAGTAC TTACTATCTA CCAGGTACTA TGCTAAGCAC      1423
CTACACACAT TATCTCATTC AATTCTGAGA GCATTTGTAT GAAGAAGGAG      1473
TAGCTATCCT CTAGAACATC AGCTCCATGA GGGCAGGGAT GTTTGTCTAT      1523
TTTGTTCACT GTTGTATCAT CAGGGCCTAG AACAGTACTT GGCACATAAT      1573
AAGTACTCAA TAAATATTTG TTGAATGAAT GAATTAACCA CGCATGATAT      1623
AGATGAAGGC CTAAGGCTCA AAGAGATGAT AGAACTTGGC CACGGTCACC      1673
CAGGCAGTAA GTGGCTGGGA TAGAAAGCAA GGACCTGCCA AATTCAGAGT      1723
CCAAGTTCTT AACCACTTAA TTCCTTCCTG TAATTACCGT TCTTTTAGTA      1773
CAGTTGCTAG TGTTGTCACT GTTATTCTTG TTGTTCCTAT TATTATTTCA      1823
GGCCCTGGGC TTGGCCAGGC AGGGAAGCCA GACACTGGAT CCCATCCTCC      1873
TCCCACCATC TCCACTTCCA TATTTCTTTC CTGCTTCCCA ACCATCCCTC      1923
TCAGTCGCCC CCGCACCACT GGCCCTTCCC ACAGCTACCA ATCCATATCC      1973
CACCCCCGCT CTTGCAG GG ATG TTC CTG ATG ACA TAC AGC CTA       2016
TCA CCA GCC TCC CAG GAG TGG CCA G GTAGGAGACG TGGAGTTGGG     2061
GGGCCAGCGG GTGGTGGAGG GAGAGATTCC ACAGGTGGAA GTGCTGGGAG      2111
GCAGAAGCAG ACCTAGGAAG TAGAAGATGC GGACAGACAG ACATTAGCTC      2161
AGTAGAGGAA AGGGTTTCCC CGGGGCCAGA GCTGTTCCAC AGTGGAAGGG      2211
GCAGCCCCAT AAAGTAAAGA GCTACCCATC ACCCGAGACG TCGTGGCAGA      2261
GGCTGTTGCA GAAGGGAGCT GAACTGCAGA TGGGAGTTCA AAAAGAGGGC      2311
CTCGAAGGAG CCTTCCACAG CCGAATTCCG GAGCTCTGCT ACTCAGGGCC      2361
TCAGTCTTCC CTCCTATTTA GTGGATGCAT CCCTGCCCCT TCTGTCCTGG      2411
GGGCTTGAGC CCTCCTGGTG CCATATGCAG CTTGGTTTCT AACAGAGGCA      2461
CACAGTGTGG TGGGGTCCGG AGGACCGTTG CCTGGGACCT GCCTTCCTTC      2511
AACCCCTCTA CCCACACCCA CACAG GT ACG GTG TGA ACC GGC TGG     2556
AAG AGA TGC TGA GGC CCT TGG TGG AAG AGG GCC TAC GCT GTG     2598
TCT TGA TCT TTG GCG TCC CCA GCA GAG TTC CCA AG              2633
GTGAAGAATC AAAGGAAGGG CTAAGAAGGG AGGTTGCCTC ACGCCCGTAA      2683
TCCCAGCACT TTGGGAGGCC AAAGTGGGTG GATCACTTGA GCCCAGGATT      2733
TTGAGACCAG CCTGGACAAC ATGGCAAAAC CCATCTCTAC AAAAAATACA      2783
AAAGTTAGCT GGGTGTGGGG GTATGTGCCT GTAGTCCCAG CTACTCGGGA      2833
GGTGGAGAGG TGGGAGGATT GCTTGAGCCC AGAAAGTCGA GGCTGCAGTG      2883
AGCCAAAATC GCGCCAGTGC ACTCTAGCCT GGGTGACAGA GCAAGACCCT      2933
GTCTCCAATA CAAACAGAAA AAGGAAGGGA GGTTGGGCAA AGGTGGACTG      2983
AGGGTCCACA CTGACTGCAC CCTCACTCCC ACATTGTGCT GGCCCTGGGG      3033
CCACAGGTGA ATGGACGTGG TCTTTGCCCT TAAGTCAGCA CCCATGTAGG      3083
GTCGGTCCTC TGTGCTTCCT TATCCAGGGG CTGTGATGAT GAAGGAAGGA      3133
GAAGGCCAGG GCTATGCTCT GTGATGGCTG TCATCCTGCC TTCCAAAGCT      3183
ACATGTAATA GACACACTGC TTTGTCCCTC CCCTGCCCCT AG G ACG        3229
AGC GGG GTT CCG CAG CTG ACT CCG AGG AGT CCC CAG CTA TTG     3271
```

```
AGG CAA TCC ATC TGT TGA GGA AGA CCT TCC CCA ACC TCC TGG              3313
TGG CCT GTG ATG TCT GCC TGT GTC CCT ACA CCT CCC ATG TCC              3355
ACT GCG GTGAGTTCCC TCCCTCCCAC CAGCCCTGCT GCCACCCACA                   3401
CTCCTACTGC CCACTTCTCA ACAGGGTGGG ACAGCCAGG GCCCAAGGTG                 3451
CTCCCCAAAA CCCAGTCATC TGTCCTGAAG GGC TCC TGA GTG AAA                  3496
ACG GAG CAT TCC GGG CTG AGG AGA GCC GCC AGC GGC TGG CTG              3538
AGG TGG CAT TGG CGT ATG CCA AGG CAG GTGAGTGAAC                        3575
CACCAGCAGG GATGGGCACC TCTGGGTCAG GAGGTGGCAG AGTGGCTAG                 3624
GAGGGCCCCA GAGTTCTGAA GGCCACCCTC TGCCCCCAG GAT GTC AGG                3673
TGG TAG CCC CGT CGG ACA TGA TGG ATG GAC GCG TGG AAG CCA              3715
TCA AAG AGG CCC TGA TGG CAC ATG GAC TTG GCA ACA GG                    3753
GTAAGGGCAG GGAATGCAGC ACAGGGCTGG CAGGAGATAG TCTGCACCAG                3803
CCCTGCCCCC GTGTCTGCTA AGAATACAG AACTGCCGGG CGTGTTGGCT                 3853
CACACCTGTA GTCCCAGCAC TTTGGGAGGC TGAGGCAGGT AGATCACTTG                3903
AGGTCAGGGG TTCAAGACCA GCCTGGCCAA CATGGTGAAA CCCCATCTCT                3953
ACTAAAAACA CAAAAATTAG CTGGGCGTGG TGGCAGGCGC CTGCAATCCC                4003
AGCTACTGGG GAGGCTGAGG CAGGAGAATC GCTTGAACCC ACGAGGCAGT                4053
GAGCTGAGAT CATGCCACTG CACTTCAGCC TGGATGACAG AGCTAGACTC                4103
CATCTCAAAA AAAAAAGAA TCACAGAACT GAAGACAGTG CTGGATGAGG                 4153
CTTTGGGGAA CCATTTAAAC CTCTGGGCCT CTGCAGGGAA ATCAAGCCCA                4203
GCACTCCAAC AGGACCAGAA CACAGGCAGT CTCCTTCCCA GCCTAGGTTC                4253
TTTCTCTCCC TGCCACATCA CCCTGGGATA CCTGGCAAGG GCCGAATAAG                4303
CCAAGACCTC CATTGTCTCC CCATAG G TAT CGG TGA TGA GCT                    4345
ACA GTG CCA AAT TTG CTT CCT GTT TCT ATG CCC TTT CCG                  4385
GTGAGCAGGG GTGGGCAGGG GTCTGCTGTG AATCCCTGCC CTTTGGCCCA                4435
AAGCTGGAGC CCACCCTGAT GACTCTGCTT TGCAG GG ATG CAG CTA                 4481
AGT CAA GCC CAG CTT TTG GGG ACC GCC GCT GCT ACC AGC TGC              4523
CCC CTG GAG CAC GAG GCC TGG CTC TCC GAG CTG TG                        4558
GTGAGTGACT AGGACTTGAG CCCCACCCTC AGCCCCTCC TAGGCACCAC                 4608
CCACATTATA CCCTCATCCC TTAG G ACC GGG ATG TAC GGG AAG                  4651
GAG CTG ACA TGC TCA TGG TGA AGC CGG AAA TGC CCT ACC TGG              4693
ACA TCG TGC GGG AGG TAA AGG ACA AG GTGAGCACAG                         4729
GTACGAGGCA AAGGGGGCTC AGGGGGCTGG ACAGAGTTT TCCACAGACT                 4779
CTGGAATCTC AGAGTTGGAA GCAGTTTGCC CTTAAGCATG CATCCTCTCC                4829
TCCCCTTCCC TGCCCAGGAA CCATCGTGGC CTTCTATGTC GGGGCTTGCA                4879
CGAGCCTCAA ACAGCCCTGC TTTAACAGTT CAAGAGTGGG CCAGGCTGCC                4929
AGCCGCAGTA ACCCAGGACA CGGGGCTCAA GATGGTCACA GATTGAGCAG                4979
GGGGGAAGGG ACGCTTCCAG AGCCACATCC ACCCTCCATT TCAGCCTGTC                5029
TCCCTGTCTG CTTCCCTGCA G C ACC CTG ACC TCC CTC TCG CCG                 5072
TGT ACC ACG TCT CTG GAG AGT TTG CCA TGC TGT GGC ATG                   5111
```

| | |
|---|---|
| GAG CCC AGG CCG GGG CAT TTG ATC TCA AGG CTG CCG TAC | 5150 |
| TGG AGG CCA TGA CTG CCT TCC GCA GAG CAG GTAGGCAGGC | 5190 |
| AAGGGTGGGG TGTTTTGACC TGCGCCACAG GGACTGATAA GCACTCTGCC | 5240 |
| TAGATCGGGG AACGACGTCC TGAGAGCTTG GGATCTTATT CCGGGAATTA | 5290 |
| CTAGTGATCT AAACAGACAC ACACTGAGGA AGAGATATGG AACTGCAGCA | 5340 |
| TAGAACACGG CCCGGTGAAG CAAGCAGAGC CCTTCATTTT TGGTTGTGAG | 5390 |
| AACGTGGCAA GCCACTTCTC TGAACCTCAG TGTCCTCACC CATAACTGGA | 5440 |
| TAACTGGGGA TAAGATACCT GGTGCGTGGT TGTCCTGAGG ATTAAATGAA | 5490 |
| GTAATATCAC TCCATAAAGG GGACTCATTT TGTTAGAATT GCACACCAGC | 5540 |
| ATGGAAGGA ACTTGCCTCT TATATTTCCT TCACTGTGCA TTTTATTCTT | 5590 |
| TGGTAAACTG AGGCCCCAAA AGAGGAAATG ACTTGCCCAA GAAATAGAGT | 5640 |
| TTCCCAAAGC TGGGCTCCGT CTCATGTGGT GTGCCCACAG GCTGTGCTTC | 5690 |
| TTCATGGTAG CCTTCTTCCC CGCCTGGCCT TCCATCGCA GAAGGTGTGC | 5740 |
| TCAGAGCTGA TCAGCGTCCC CCCAGCAACT TTCTGCATCT CTCCCAACAC | 5790 |
| AG GTG CTG ACA TCA TCA TCA CCT ACT ACA CAC CGC AGC TGC | 5831 |
| TGC AGT GGC TGA AGG AGG AAT GAT GGA GAC AGT GCC AGG CCC | 5873 |
| AAG AAC TAG AAC TTT AAA ACG TTC CCG GGG CCT CAG ACA AGT | 5915 |
| GAA AAC CAA AGT AAA TGC TGC TTT TAG AAC TGT GCCCTCATGC | 5958 |
| CCTCTTCCTG CTCACATGCT AGCGGGGCCC AGCAGCCCTG GGTGGTTTTG | 6008 |
| CCAGCATGCT AACTCTTGTA ACTCGCAGCT GCATCCTATG AGCTCTCCA | 6058 |
| AGCTT | 6063 |

( 2 ) INFORMATION FOR SEQ ID NO: 5:

( i ) SEQUENCE CHARACTERISTICS:
        ( A ) LENGTH: 20
        ( B ) TYPE: NUCLEIC ACID
        ( C ) STRANDEDNESS: SINGLE
        ( D ) TOPOLOGY: LINEAR ( i i ) MOLECULE TYPE:
        ( A ) DESCRIPTION: OTHER/SYNTHETIC ( i i i ) HYPOTHETICAL: NO ( i v ) ANTI-SENSE: NO ( x ) PUBLICATION INFORMATION: NONE ( x i ) SEQUENCE DESCRIPTION: SEQ ID NO:5:

| AGACAGACAT TAGCTCAGTA | 20 |
|---|---|

( 2 ) INFORMATION FOR SEQ ID NO: 6:

( i ) SEQUENCE CHARACTERISTICS:
        ( A ) LENGTH: 20
        ( B ) TYPE: NUCLEIC ACID
        ( C ) STRANDEDNESS: SINGLE
        ( D ) TOPOLOGY: LINEAR ( i i ) MOLECULE TYPE:
        ( A ) DESCRIPTION: OTHER/SYNTHETIC ( i i i ) HYPOTHETICAL: NO ( i v ) ANTI-SENSE: NO (x) PUBLICATION INFORMATION: NONE (xi) SEQUENCE DESCRIPTION: SEQ ID NO: 6:

GGCAAAGACC ACGTCCATTC                                                                 20

METHODS FOR DETERMINING SUSCEPTIBILITY TO LEAD POISONING

This application is a division of Ser. No. 08/195,744 filed Feb. 14, 1994 which issued as U.S. Pat. No. 5,639,607 on Jun. 17, 1997 which is a continuation of U.S. Ser. No. 07/742,130 filed Aug. 7, 1991, abandoned.

This invention was supported by National Institute of Health grants DK34045 and DK26824. The government may have certain rights in the invention.

SPECIFICATION

1. Field of the Invention

This invention relates to a method for determining susceptibility to lead poisoning by assaying for a polymorphism in the gene encoding 6-amino levulinate dehydratase (ALA-D), as well as a diagnostic kit for determining the polymorphism comprising a means for extracting a DNA sample and a means for detecting the presence of the ALA-D polymorphism in the DNA sample.

2. Background of the Invention

Lead is toxic to numerous organ systems, including the reticuloendothelial and nervous systems. The most important consequence of low-level lead toxicity is irreversible neurological damage. Although ambient lead levels are markedly below those of a decade ago as a result of the reduced use of leaded gasoline, there remain the problems of widespread detection of lead-paint poisoning of children, control of lead exposure in the workplace, increased lead absorption and low-level lead toxicity.

Recent neuroepidemiologic studies have demonstrated peripheral neurological abnormalities in lead-exposed adults at levels of 30–40 µg/dl and in children at blood lead levels as low as 20–30 µg/dl. Seppalainen et al. (1983) Neurotoxicology, 4:181–192; and Needleman et al. (1979) N. Eng. J. Med., 300:689–695. The Second National Health and Nutrition Examination Survey (NHANES-II) found that 1.5 million preschool children had blood lead levels of 25 µg/dl and above, indicating lead absorption.

Recent evidence indicates that the prevalence of central neurological symptoms is elevated and neurobehavioral performance is impaired in adults at blood lead levels of 40–60 µg/dl. Baker et al. (1985) Brit. J. Industr. Med., 41:507–516; Jeyarathnam et al. (1987) Brit. J. Industr. Med., 43:626–629; and Lilis et al. (1985) Arch. Env. Health, 40:38–47. Central nervous system dysfunction in children with elevated blood lead levels has been measured using verbal I.Q. test scores. In one U.S. study, children with blood lead levels of 25–45 µg/dl scored 4.5 points lower on the I.Q. tests after adjusting for parental education, childhood illnesses and socioeconomic status. Needleman et al. (1979). In two cross-sectional European studies, similar effects of low-level lead central nervous system toxicity were observed. Winneke et al. (1981) Internat. Conf. on Heavy Metals in the Environment, Geneva, World Health Organization, pp. 553–556; and Smith et al. (1983) Dev. Med. Child Neurol., 25(suppl 47):1–20. Furthermore, both decreases in intelligence and shortened attention span have been reported in young children who had moderately elevated umbilical cord blood lead levels at birth. Bellinger et al. (1987) N. Engl. J. Med., 316:1037–1043. By all measurements, children appear to be at significant risk from low-level lead exposure. Needleman et al., (1990) N. Engl. J. Med., 322:83–88.

In a rat model, lead has been shown to be mobilized from maternal stores during pregnancy and to cross the placenta. Moreover, lead has been shown to produce neural tube defects in three rodent species. Gerber et al. (1977) Mutat. Res., 76:115–141. In man, increased placental lead concentrations have been reported in stillborns and in infants with mental retardation and congenital anomalies. Wibberly et al. (1977) J. Med. Genet., 14:339–345. A study of over 5000 births with 3% congenital malformations demonstrated a significant dose-related correlation between placental lead concentration and congenital anomalies. Needleman et al. (1984) J. Amer. Med. Assoc., 251:2956–2959. The effects of other possible teratogenic variables were eliminated by multivariant analysis.

There is also evidence that lead affects the male gamete. Increased numbers of chromosomal aberrations in sperm have been found both in experimental animals exposed to lead and in lead workers. Deknudt et al. (1973) Environ. Physiol. Biochem., 3:132–138. Lead was one of only three substances included on the initial California "short list" of reproductive toxins. Baum. Chem. Eng. News, Mar. 16, 1987, p. 22.

ALA-D, the second enzyme in the heme biosynthetic pathway, catalyzes the asymmetric condensation of two molecules of 5-aminolevulinate (ALA) to form the monopyrrole, porphobilinogen (PBG), the precursor of heme, cytochromes and cobalamins. The mammalian enzyme has been purified to homogeneity from bovine liver and human erythrocytes. Wu et al. (1974) Proc. Natl. Acad. Sci. USA, 71:1767–1770; Gurne et al. (1977) Proc. Natl. Acad. Sci. USA, 74:1383–138; and Anderson and Desnick (1979) J. Biol. Chem., 254:6924–6930. ALA-D is a metalloenzyme composed of eight identical subunits and eight zinc atoms. Anderson and Desnick (1979); Bevan et al. (1980) J. Biol. Chem., 255:2030–2035; Tsukamoto et al. (1979) Biochem. Biophys. Acta, 570:167–178; Tsukamoto et al. (1980) Int. J. Biochem., 12:751–756; and Jaffe et al. (1984) J. Biol. Chem., 259:5032–5036.

ALA-D activity is inhibited by lead and various heavy metals as well as by the oxidation of critical thiol groups. Anderson & Desnick (1979); and Jordan et al. (1985) Biochem. J., 222:1015–1020. Lead atoms replace the zinc atoms which are required to maintain ALA-D activity. Tsukamoto et al. (1979). The inhibition of erythrocyte ALA-D activity has been used as a sensitive diagnostic indicator of lead exposure. Morgan et al. (1972) Arch. Intern. Med., 130:335–341. The inhibition is stoichiometric; e.g., 15 and 30 µg of Pb per dl blood results in 50% and 75% ALA-D inhibition, respectively. More recently, the ratio of ALA-D present before and after reactivation with zinc and DTT has been shown to correlate best to blood lead levels. Chisholm et al. (1985), Clin. Chem., 31:662–668. The inhibition of ALA-D activity results in a proportionate accumulation of ALA blood and urine. The accumulation of ALA has been causally related to the neurological manifestations of lead poisoning.

Human ALA-D, has been shown to be a polymorphic enzyme. Petrucci et al. (1982) Hum. Genet., 60:289–290; and Battistuzzi et al. (1981) Ann. Hum. Genet., 45:223–229. The allelic polypetides are encoded by a gene located on chromosome 9 in the region 9q34. Potluri et al. (1987) Hum. Genet., 76:236–239. The ALA-D gene has two common alleles, ALA-D[1] and ALA-D[2], which result in a polymorphic enzyme system with three distinct charge isozyme phenotypes, designated ALA-D 1-1, ALA-D 1-2 and ALA-D 2-2. The isozymes may be separated by starch gel electrophoresis. Battistuzzi (1981). In the Italian population, the frequencies of the isozyme phenotypes are 1-1 (81%), 1-2 (17%) and 2-2 (2%), consistent with gene frequencies of 0.90 and 0.10 for the ALA-D$^1$ and ALA-D$^2$ alleles, respectively. Similar results were obtained in other European populations, whereas expression of the ALA-D$^2$ allele was not observed in a large sample of Black individuals from Liberia. Benkmann et al. (1983) Hum. Hered., 33:62–64. A study of ALA-D isozyme phenotypes in erythrocytes of over 950 normal Caucasian individuals from New York showed the frequencies of the ALA-D 1-1, 1-2, and 1-2 isozyme phenotypes to be similar to those observed in the Italian population.

The occurrence of the ALA-D polymorphism is of interest, particularly with respect to the possible increased susceptibility of certain isozyme phenotypes to the detrimental effects of lead exposure. Polymorphisms at other genetic loci are known to be related to differential inherited responses to environmental challenges. For example, the response to Plasmodium (malaria) is affected by hemoglobin S, hemoglobin AS heterozygotes being more resistant to disease than individuals with normal hemoglobin AA. Pasval et al, (1978) Nature, 274:7801–7803. Similarly, Asian individuals are more susceptible to alcohol intoxication due to the presence of a particular alcohol dehydrogenase polymorphism. Propping (1978) J. Physiol. Biochem. Pharmacol., 83:124–173.

The existence of this common ALA-D polymorphism and the fact that ALA-D is markedly inhibited by lead suggests that there is a physiologic relationship between the frequency of the ALA-D$^2$ allele and lead poisoning. For instance, individuals with the ALA-D$^2$ allele may be more susceptible to the detrimental effects of lead exposure if the ALA-D$^2$ subunit bound lead more tightly than the ALA-D$^1$ subunit. They would have higher blood and bone lead concentrations as well as higher total body lead stores, making them even more likely to express subclinical and clinical manifestations of chronic low level or acute lead exposure. Alternatively, the tight binding of blood lead by erythrocyte ALA-D$^2$ may prevent the distribution of lead to the neurologic system, thereby preventing or minimizing the neurotoxic effects of lead.

A study of blood lead levels and ALA-D isozyme types in 1277 blood samples obtained from the New York City Lead Screening Program was performed in a double-blind fashion. That is, the blood lead levels were provided by the Toxicology Laboratory only after the blind determination of the ALA-D isozyme phenotype. Table I is a compilation of the number of individuals with the ALA-D 1-1, ALA-D 1-2, ALA-D 2-2 phenotypes having blood lead levels above or below either 25 or 30 μg/dl. These results demonstrate that a high proportion of these individuals with high blood lead levels had the ALA-D$^2$ allele. Astrin et al. (1987) Ann. N. Y. Acad. Sci., 514:23–29. The presence of the ALA-D$^2$ allele apparently leads to approximately a two-fold increase in lead retention at blood levels of 25 or 30 μg/dl. In some cases, the ethnic group was known. The incidence of the ALA-D$^2$ allele among lead poisoned Black children was high even though the incidence of the ALA-D$^2$ allele among Blacks in general is low. The results obtained support a relationship between the ALA-D$^2$ allele and the accumulation of lead in the blood. Similar data support the identical conclusion. Ziemsen et al. (1986) Int. Arch. Occup. Environ. Health, 58:245–247.

TABLE 1

HUMAN ALA-D POLYMORPHISM: ASSOCIATION WITH LEAD POISONING

| Sample Set | Blood Lead Level (μg/dl) | ALA-D Isozyme Phenotype (Number and Percent in Sample Set) | | | | |
|---|---|---|---|---|---|---|
| | | Total | 1-1 | (%) | 1-2 or 2-2 | |
| Total: | <25 | 870 | 803 | (71) | 67 | (47) |
| | ≥25 | 408 | 333 | (29) | 75 | (53) |
| | | 1278 | 1136 | (100) | 142 | (100) |
| | >30 | 1000 | 919 | (81) | 81 | (57) |
| | ≥30 | 278 | 217 | (19) | 60 | (43) |
| | | 1278 | 1136 | (100) | 142 | (100) |
| Blacks: | >30 | 292 | 282 | (88) | 10 | (38) |
| | ≥30 | 53 | 37 | (12) | 16 | (62) |
| | | 345 | 319 | (100) | 26 | (100) |

It has previously been found that the frequency of the ALA-D$^2$ allele to be 10–11% in Italian and German populations. Battistuzzi et al. (1981) "δ-aminolevulinate Dehydratase: A new Genetic Polymorphism in Man", Ann. Hum. Genet., 45:223–229; and Benkmann et al., (1983) "Polymorphism of Delta-aminolevulinic Acid Dehydratase in Various Populations", Hum. Hered., 33:62–64. A study indicated an ALA-D$^2$ allele frequency of 20% in Eastern European Ashkenazi Jews living in Israel. Ben-Ezzer et al., (1987) "Genetic Polymorphism of Delta-aminolevulinate Dehydratase in Several Population Groups in Israel", Hum. Hered., 37:229–232. The blood samples used for this study came from a Tay-Sachs screening program, which would be biased toward an Ashkenazi Jewish population. In this experiment the observed ALA-D$^2$ allele frequency of 12% was thus somewhat higher than the average frequency of 10–11% in European populations.

It would be useful to have a rapid, inexpensive diagnostic method to detect the human ALA-D polymorphism. Such a method is useful in screening for persons susceptible to lead poisoning so that they could be given jobs with less exposure to lead. Also, screening may identify children who are more susceptible to lead poisoning and therefore dictate a more rigorous prevention program, monitoring and/or detoxification therapy in such children.

SUMMARY OF THE INVENTION

A diagnostic method for determining susceptibility to lead poisoning by obtaining a biological sample from a patient and analyzing the sample for the presence of a polymorphism of the δ-amino levulinate dehydratase gene. Suitable analysis methods include but are not limited to digesting the DNA with a restriction endonuclease that recognizes the DNA sequence at the site of the polymorphism being able to cleave at the site in the ALA-D$^2$ but not the ALA-D$^1$ allele, and determining whether the DNA sample has been cleaved by the restriction endonuclease. The DNA encoding ALA-D may be amplified prior to restriction endonuclease cleavage.

The invention is useful for screening biological samples with a high degree of reliability and specificity. Samples include but are not limited to body fluids such as blood, sera, and tissue samples. A diagnostic kit is provided to perform the method of the present invention. The kit provides a means for extracting DNA from the sample, means for digesting the DNA and a means for analyzing the digestion products. A means for amplifying the DNA encoding ALA-D or a portion thereof may also be provided.

DETAILED DESCRIPTION OF THE INVENTION

Figure 1:
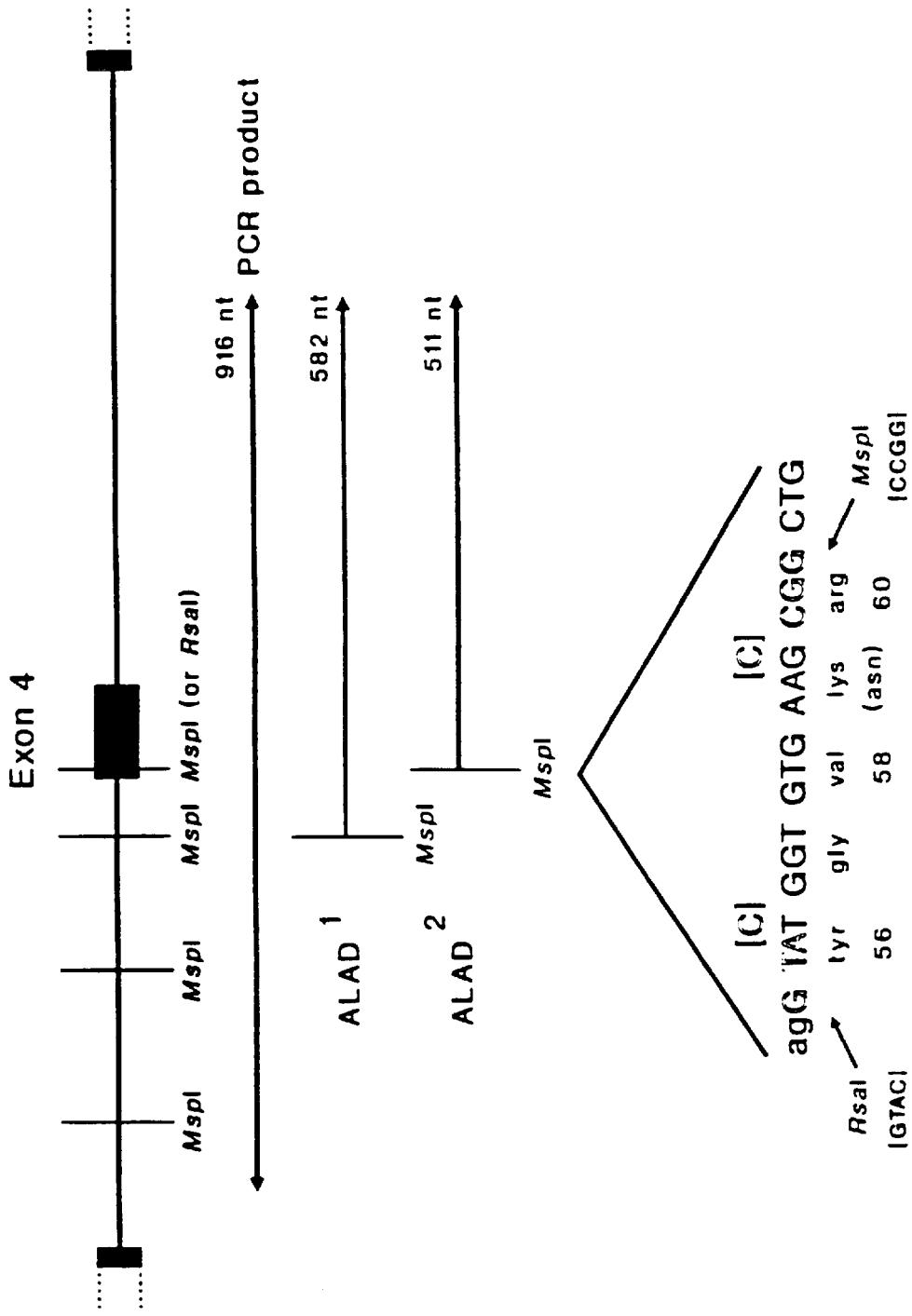
FIG. 1 shows a schematic for the PCR analysis of the ALA-D polymorphism.

The molecular nature of the ALA-D polymorphism has now been determined to be based upon the single nucleotide difference found between the sequences of the ALA-D$^1$ and ALA-D$^2$ cDNA clones. Codon 59 is AAG (lysine) in ALA-D$^1$ and AAC (asparagine) in ALA-D$^2$. This transversion results in a new restriction endonuclease site CCGG in ALA-D$^2$ cDNA and in ALA-D$^2$ genomic DNA thus allowing differential restriction endonuclease digestion. A particularly suitable restriction endonuclease for use in the present invention is Msp I, however, any restriction endonuclease capable of recognizing the nucleotides CCGG or a DNA sequence containing the nucleotides CCGG so as to cleave the DNA at the CCGG site or any other detectable site upon recognition of CCGG is suitable for use in the present invention. The segment of DNA encoding ALA-D or a segment thereof may be amplified prior to restriction by the endonuclease. In the preferred embodiment of the present invention, the pertinent DNA sequence is amplified prior to restriction endonuclease digestion.

The amplification may be carried out by synthesizing DNA fragments using a polymerase chain based reaction such as that shown in FIG. 1. Any other method of DNA amplification is suitable for use in the present invention provided it is reasonably accurate and maintains reasonable fidelity of the DNA sequence. Preferably, primers are prepared based on the DNA sequence in the introns surrounding exon 4, the site of the transversion. Preferably the primers are chosen so as to span other CCGG restriction endonuclease sites, as an internal control, so that unique cleavage products result for both the ALA-D$^1$ and ALA-D$^2$ allele. For instance sets of DNA primers for the 5' intron having the nucleotide sequence

SEQ ID NO: 1    5'AGACAGACATTAGCTCAGTA3' and for the 3' intron

SEQ ID NO: 2    5'GGCAAAGACCACGTCCATTC3' are preferred.

After amplification, the DNA is digested by the restriction endonuclease recognizing the CCGG DNA sequence. The resultant DNA segments are analyzed for example by electrophoresis on an agarose gel and subsequent fluorographic visualization by staining the DNA with intercalating agents such as ethidium bromide.

Also included in the present invention are any other suitable methods for detecting the polymorphism. Such methods include but are not limited to allele-specific oligonucleotide hybridization, oligonucleotide ligation, ligation amplification and competitive PCR. Conner et al. (1983) Proc. Natl. Acad. Sci. USA, 80:278–282; Saiki et al. (1985) Nature, 324:163–166; Chehab et al. (1987) Nature, 329:293–294; Lungren et al. (1988) Science, 241:1077–1080; Wu et al. (1989) Proc. Natl. Acad. Sci. USA, 86:2757–2760; and Wu et al. (1989) Genomics, 4:560–569.

The present invention also provides a kit for determining a polymorphism in the ALA-D gene comprising a means for extracting DNA from a sample obtained from humans, and means for detecting the presence or absence of ALA-D$^2$ allele in the DNA sample. In addition, the kit may further comprise a means for amplifying the gene encoding ALA-D or a part thereof.

Also included in the present invention are recombinant DNA molecules encoding ALA-D$^1$ and ALA-D$^2$ and any portion of the ALA-D$^1$ and ALA-D$^2$ sequence. Thus, the invention includes any sequence of human ALA-D, including the use of primers that involve intronic sequences. For example, ALA-D$^1$ or ALA-D$^2$ sequences involving any domains such as the active site, or any part thereof, the zinc binding site, etc. The complete cDNA sequence of human ALA-D$^2$ is shown in Table 2. The ALA-D$^1$ sequence differs only by the presence of a G in the third position of codon 59, thereby encoding a lysine residue in position 59 of the ALA-D$^1$ polypeptide. The invention also includes a recombinant vector containing some or all of the genomic DNA encoding ALA-D$^2$. The nucleotide sequence of the genomic DNA containing all coding exons of ALA-D$^2$ is shown in Table 3. In Table 3, all the coding exons are shown in upper case letters whereas the introns are shown in lower case letter.

The invention further encompasses DNA vectors into which the gene has been cloned and expression systems into which the recombinant vectors have been transferred. Suitable vectors include but are not limited to plasmids, viruses and retroviruses. Suitable expression systems include but are not limited to bacteria, fungi, mamalian cell lines, plant cell lines, insect cell lines and transgenic non-human mammals.

Preferably, the recombinant vectors contain an oligonucleotide having some or all of the sequences as shown in Tables 2 and 3.

TABLE 2

THE COMPLETE CDNA SEQUENCE OF HUMAN ALA-D2

SEQ ID NO: 3

| | |
|---|---|
| GAGACCGGAG CGGGAGACAG CGGTGACAGG AGCAGCGGCC GGGAGCCCTT | 50 |
| AGGGAGGCAG ACAGAGCCTG CAGCCAATGC CCCAGGAGCC CTCGGTTCCA | 100 |
| ACCAACTGAT GCCCCTGTGC CCACTGGCCC ACGCC ATG CAG CCC CAG | 147 |
| TCC GTT CTG CAC AGC GGC TAC TTC CAC CCA CTA CTT CGG GCC | 189 |
| TGG CAG ACA GCC ACC ACC ACC CTC AAT GCC TCC AAC CTC ATC | 231 |
| TAC CCC ATC TTT GTC ACG GAT GTT CCT GAT GAC ATA CAG CCT | 273 |
| ATC ACC AGC CTC CCA GGA GTG GCC AGG TAT GGT GTG AAC CGG | 315 |
| CTG GAA GAG ATG CTG AGG CCC TTG GTG GAA GAG GGC CTA CGC | 357 |
| TGT GTC TTG ATC TTT GGC GTC CCC AGC AGA GTT CCC AAG GAC | 399 |
| GAG CGG GGT TCC GCA GCT GAC TCC GAG GAG TCC CCA GCT ATT | 441 |
| GAG GCA ATC CAT CTG TTG AGG AAG ACC TTC CCC AAC CTC CTG | 483 |
| GTG GCC TGT GAT GTC TGC CTG TGT CCC TAC ACC TCC CAT GGT | 525 |
| CAC TGC GGG CTC CTG AGT GAA AAC GGA GCA TTC CGG GCT GAG | 567 |

TABLE 2-continued

THE COMPLETE CDNA SEQUENCE OF HUMAN ALA-D2

SEQ ID NO: 3

| | |
|---|---:|
| GAG AGC CGC CAG CGG CTG GCT GAG GTG GCA TTG GCG TAT GCC | 609 |
| AAG GCA GGA TGT CAG GTG GTA GCC CCG TCG GAC ATG ATG GAT | 651 |
| GGA CGC GTG GAA GCC ATC AAA GAG GCC CTG ATG GCA CAT GGA | 693 |
| CTT GGC AAC AGG GTA TCG GTG ATG AGC TAC AGT GCC AAA TTT | 735 |
| GCT TCC TGT TTC TAT GGC CCT TTC CGG GAT GCA GCT AAG TCA | 777 |
| AGC CCA GCT TTT GGG GAC CGC CGC TGC TAC CAG CTG CCC CCT | 819 |
| GGA GCA CGA GGC CTG GCT CTC CGA GCT GTG GAC CGG GAT GTA | 861 |
| CGG GAA GGA GCT GAC ATG CTC ATG GTG AAG CCG GGA ATG CCC | 813 |
| TAC CTG GAC ATC GTG CGG GAG GTA AAG GAC AAG CAC CCT GAC | 945 |
| CTC CCT CTC GCC GTG TAC CAC GTC TCT GGA GAG TTT GCC ATG | 987 |
| CTG TGG CAT GGA GCC CAG GCC GGG GCA TTT GAT CTC AAG GCT | 1029 |
| GCC GTA CTG GAG GCC ATG ACT GCC TTC CGC AGA GCA GGT GCT | 1071 |
| GAC ATC ATC ATC ACC TAC TAC ACA CCG CAG CTG CTG CAG TGG | 1113 |
| CTG AAG GAG GAA TGA TGGAGACAGT GCCAGGCCCA AGAACTAGAA | 1158 |
| CTTTAAAACG TTCCCGGGGC CTCAGACAAG TGAAAACCAA AGTAAATGCT | 1208 |
| GCTTTTAGAA CTGT | 1222 |

TABLE 3

THE COMPLETE GENOMIC DNA SEQUENCE OF ALA-D2

SEQ ID NO: 4

```
-600  gagaccatcc tgggaagcat ggcaagacct ccatctctac aaaaaattcg
-550  aaaattagct ggatgttgtg gtgcacacct gcagtcccag ctacttggga
-500  ggctgagttg ggagaaacag ttgagcccgg gaggtcaagg ctgcagtgag
-450  tcgagattgc accactgcac tccagcctgg gcgacagaga ccctgtgtga
-400  aaaaaaaaaa aagaagagaa ttttttttaa acagtcattg cttgctcaga
-350  tgtttacttt aaaagataat aatgaacaag aagcagtcac ataaaataca
-300  agcccaaatt ttatatcatt agattctgat tgtcatgaaa gtttctaaag
-250  acttacttc  atttctcaac ttaccttgtt gaccagcagg gattggtgaa
-200  ccaggctgtg agtagcattg ggctagagag aggggaggca ggaatctaga
-150  agagctgttt tccagatgtg accatctcct gaggacaggg accatgtcct
-100  atgtgccacc catcaccccc cacagACAGA GCCTGCAGCC AATGCCCCAG
 -50  GAGCCCTCGG TTCCAACCAA CTGATGCCCC TGTGCCCACT GGCCCACGCC
   1  ATGCAGCCCC AGTCCGTTCT GCACAGCGGG TACTTCCACC CACTACTTCG
  51  GGCCTGGCAG ACAGCCACCA CCACCCTCAA TGCCTCCAAC CTCATCTACC
 101  CCATCTTTGT CACgtgagtc tccaagaatg ggcaggcct ctgctctgct
 151  ggttggggtt ggggttgggg agggagtgtt gactggagcg ggcatcagta
 201  tggctggggg tggcaaagtg agctgtcagc ttgaaattca aggcactgga
 251  agcaggctac ttggattaag gacaggaatc ttaggaacaa aacaaacttt
 301  gaaagaactc attcatccca tttggaaaat tagaagaata acccttgcct
 351  gccatcctga gctcttgcag taagacagaa gctgagaagg tgctctgtac
 401  attgtaaagt gctatgtacc tgtaagagat ggcagtcatt gaggctgggc
 451  acggtggctc acgcctgtaa tcccagcact ttgggaggct gaggcaggcg
 501  gatcacgagg tcaggagatc gagaccatcc tggctaatat ggtgaaaccc
 551  tgtctctact aaaaacacaa agaaattagc caggcgtggt ggcgggtgcc
 601  tgtagtccca gctacttggg aggctgaggc aggagaatgg cgtgaacccg
 651  ggaggcggag cttgcagtga gccgagattg caccacttca ctccagcctg
 701  ggcgacagag ccagactcca tctcaaaaaa aaaaaaaaaa aaaagagatg
 751  gcaatcgtga ttgttaataa taatgcagac atttactgag tacttactat
 801  ctaccaggta ctatgctaag cacctacaca cattatctca ttcaattctg
 851  agagcatttg tatgaagaag gagtagctat cctctagaac atcagctcca
 901  tgagggcagg gatgtttgtc tattttgttc actgttgtat catcagggcc
 951  tagaacagta cttggcacat aataagtact caataaatat ttgttgaatg
1001  aatgaattaa ccacgcatga tatagatgaa ggcctaaggc tcaaagagat
1051  gatagaactt ggccacggtc acccaggcag taagtggctg ggatagaaag
1101  caaggacctg ccaaattcag agtccaagtt cttaaccact taattccttc
1151  ctgtaattac cgttctttta gtacagttgc tagtgttgtc actgttattc
1201  ttgttgttcc tattattatt tcaggccctg ggcttggcca ggcagggaag
1251  ccagacactg gatcccatcc tcctcccacc atctccactt ccatatttct
1301  ttcctgcttc ccaaccatcc ctctcagtcg ccccccgcacc actggcccct
1351  cccacagcta ccaatccata tcccacccc gctcttgcag GGATGTTCCT
1401  GATGACATAC AGCCTATCAC CAGCCTCCCA GGAGTGGCCA Ggtaggagac
1451  gtggagttgg ggggccagcg ggtggtggag ggagagattc cacaggtgga
1501  agtgctggga ggcagaagca gacctaggaa gtagaagatg cggacagaca
1551  gacattagct cagtagagga aagggttttcc ccggggccag agctgttcca
1601  cagtggaagg ggcagcccca taagtaaag agctaccat cacccgagac
1651  gtcgtggcag aggctgttgc agaagggagc tgaactgcag atgggagttc
1701  aaaaagaggg cctcgaagga gccttccaca gccgaattcc ggagctctgc
1751  tactcagggc ctcagtcttc cctcctattt agtggatgca tccctgcccc
1801  ttctgtcctg ggggcttgag ccctcctggt gccatatgca gcttggtttc
```

TABLE 3-continued

THE COMPLETE GENOMIC DNA SEQUENCE OF ALA-D2

SEQ ID NO: 4

```
1851  taacagaggc acacagtgtg gtggggtccg gaggaccgtt gcctgggacc
1901  tgccttcctt caaccectct acccacaccc acacagGTAC GGTGTGAACC
1951  GGCTGGAAGA GATGCTGAGG CCCTTGGTGG AAGAGGGCCT ACGCTGTGTC
2001  TTGATCTTTG GCGTCCCCAG CAGAGTTCCC AAGgtgaaga atcaaaggaa
2051  gggctaagaa gggaggttgc ctcacgcccg taatcccagc actttgggag
2101  gccaaagtgg gtggatcact tgagcccagg attttgagac cagcctggac
2151  aacatggcaa aacccatctc tacaaaaaat acaaaagtta .gctgggtgtg
2201  ggggtatgtg cctgtagtcc cagctactcg ggaggtggag aggtgggagg
2251  attgcttgag cccagaaagt cgaggctgca gtgagccaaa atcgcgccag
2301  tgcactctag cctgggtgac agagcaagac cctgtctcca atacaaacag
2351  aaaaaggaag ggaggttggg caaaggtgga ctgagggtcc acactgactg
2401  caccctcact cccacattgt gctggccctg gggccacagg tgaatggacg
2451  tggtctttgc ccttaagtca gcacccatgt agggtcggtc ctctgtgctt
2501  ccttatccag gggctgtgat gatgaaggaa ggagaaggcc agggctatgc
2551  tctgtgatgg ctgtcatcct gccttccaaa gctacatgta.atagcacac
2601  tgctttgtcc ctcccctgcc cctagGACGA GCGGGGTTCC GCAGCTGACT
2651  CCGAGGAGTC CCCAGCTATT GAGGCAATCC ATCTGTTGAG GAAGACCTTC
2701  CCCAACCTCC TGGTGGCCTG TGATGTCTGC CTGTGTCCCT ACACCTCCCA
2751  TGGTCACTGC Ggtgagttcc ctccctccca ccagccctgc tgccacccac
2801  actcctactg cccacttctc aacagggtgg ggacagccag ggcccaaggt
2851  gctccccaaa acccagtcat ctgtcctgaa gGGCTCCTGA GTGAAAACGG
2901  AGCATTCCGG GCTGAGGAGA GCCGCCAGCG GCTGGCTGAG GTGGCATTGG
2951  CGTATGCCAA GGCAGgtgag tgaaccacca gcagggatgg gcacctctgg
3000  gtcaggaggt ggcagagtgg ctaggagggc cccagagttc tgaaggccac
3051  cctctgcccc ccagGATGTC AGGTGGTAGC CCCGTCGGAC ATGATGGATG
3101  GACGCGTGGA AGCCATCAAA GAGGCCCTGA TGGCACATGG ACTTGGCAAC
3151  AGGgtaaggg cagggaatgc agcacagggc tggcaggaga tagtctgcac
3201  cagccctgcc cccgtgtctg ctaagaatca cagaactgcc gggcgtgttg
3251  gctcacacct gtagtccag cactttggga ggctgaggca ggtagatcac
3301  ttgaggtcag gggttcaaga ccagcctggc caacatggtg aaacccccatc
3351  tctactaaaa acacaaaaat tagctgggcg tggtggcagg cgcctgcaat
3401  cccagctact ggggaggctg aggcaggaga atcgcttgaa cccacgaggc
3451  agtgagctga gatcatgcca ctgcacttca gcctggatga cagagctaga
3501  ctccatctca aaaaaaaaaa gaatcacaga actgaagaca gtgctggatg
3551  aggctttggg gaaccattta aacctctggg cctctgcagg gaaatcaagc
3601  ccagcactcc aacaggacca gaacacaggc agtctcctc ccagcctagg
3651  ttctttctct ccctgccaca tcaccctggg atacctggca agggccgaat
3701  aagccaagac ctccattgtc tcccccatagG TATCGGTGAT GAGCTACAGT
3751  GCCAAATTTG CTTCCTGTTT CTATGGCCCT TTccGgtgag caggggtggg
3801  cagggtctg ctgtgaatcc ctgcccttg gcccaaagct ggagcccacc
3851  ctgatgactc tgctttgcag GGATGCAGCT AAGTCAAGCC CAGCTTTTGG
3901  GGACCGCCGC TGCTACCAGC TGCCCCCTGG AGCACGAGGC CTGGCTCTCC
3951  GAGCTGTGgt gagtgactag gacttgagcc ccaccctcag cccctcta
4001  ggcaccaccc acattatacc ctcatcccctt agGACCGGGA TGTACGGGAA
4051  GGAGCTGACA TGCTCATGGT GAAGCCGGGA ATGCCCTACC TGGACATCGT
4101  GCGGGAGGTA AAGGACAAGg tgagcacagg tacgaggcaa aggggggctca
4151  ggggctggg acagagttt ccacagactc tggaatctca gagttggaag
4201  cagtttgccc ttaagcatgc atcctctcct cccttcct gcccaggaac
4251  catcgtggcc ttctatgtcg gggcttgcac gagcctcaaa cagccctgct
4301  ttaacagttcaagagtgggc caggctgcca gccgcagtaa cccaggacac
4351  ggggctcaag atggtcacag attgagcagg ggggaaggga cgcttccaga
4401  gccacatcca ccctccattt cagcctgtct ccctgtctgc ttccctgcag
4451  CACCCTGACC TCCCTCTCGC CGTGTACCAC GTCTCTGGAG AGTTTGCCAT
4501  GCTGTGGCAT GGAGCCCAGG CCGGGGCATT TGATCTCAAG GCTGCCGTAC
4551  TGGAGGCCAT GACTGCCTTC CGCAGAGCAG gtaggcaggc aagggtgggg
4601  tgttttgacc tgcgccacag ggactgataa gcactctgcc tagatcgggg
4651  aacgacgtcc tgagagcttg ggatcttatt ccgggaatta ctagtgatct
4701  aaacagacac acactgagga agagatatgg aactgcagca tagaacacgg
4751  cccggtgaag caagcagagc ccttcatttt tggttgtgag aacgtggcaa
4801  gccacttctc tgaacctcag tgtcctcacc cataactgga taactgggga
4851  taagatacct ggtgcgtggt tgtcctgagg attaaatgaa gtaatatcac
4901  tccataaagg ggactcattt tgttagaatt gcacaccagc atgggaagga
4951  acttgcctct tatatttcct tcactgtgca ttttattctt tggtaaactg
5001  aggccccaaa agaggaaatg acttgcccaa gaaatagagt ttcccaaagc
5osl  tgggctccgt ctcatgtggt gtgcccacag gctgtgcttc ttcatggtag
5101  ccttcttccc cgcctggcct tcccatcgca gaaggtgtgc tcagagctga
5151  tcagcgtccc cccagcaact ttctgcatct ctcccaacac agGTGCTGAC
5201  ATCATCATCA CCTACTACAC ACCGCAGCTG CTGCAGTGGC TGAAGGAGGA
5251  ATGATGGAGA CAGTGCCAGG CCCAAGAACT AGAACTTTAA AACGTTCCCG
5301  GGGCCTCAGA CAAGTGAAAA CCAAAGTAAA TGCTGCTTTT AGAACTGTgc
5351  cctcatgccc tcttcctgct cacatgctag cggggcccag cagccctggg
5401  tggttttgcc agcatgctaa ctcttgtaac tcgcagctgc atcctatgag
5451  ctctcccaag ctt
```

Methods of cloning genes in the proper orientation and with the proper flanking sequences, transforming the genes into a suitable host cell and expressing and purifying the proteins are known in the art and examples are provided below. Detailed DNA cloning methods are provided in a variety of sources. See e.g. Sambrook et al., Molecular Cloning A Laboratory Manual, Cold Spring Harbor Laboratory Press, NY, (1989).

Gene transfer into an expression system can be accomplished by any of the well known means in the art. For example, methods of gene transfer include but are not limited to $CaCl_2$ mediated transfection and electroporation in the case of bacteria, and in the case of eukaryotic cells, $CaPO_4$ mediated transfection, viral infection including retroviral latent infection, electroporation, liposome mediated DNA transfer and microinjection among others.

A transgenic non-human mammal, for instance a mouse, carrying either the human ALA-$D^1$ or ALA-$D^2$ allele can be used as a model system to determine and compare the contribution of the ALA-D polymorphism to the pathophysiology of lead poisoning, for example, extent of lead uptake, tissue-specific distribution of lead, and tissue-specific inhibition of ALA-D by lead.

In an embodiment of this invention a transgenic mammal in which a substantial portion of its germ and somatic cells contain a recombinant activated human ALA-$D^1$ or ALA-$D^2$ sequence can be produced as follows.

For the purposes of gene transfer experiments, the complete ALA-$D^1$ and ALA-$D^2$ genomic sequence including 2.1 kilobase pair (kb) of 5' untranslated sequence should be used. C57BL/6 mice, whose haploid genome contains only one copy of the mouse ALA-D gene, can be used as sources of eggs and sperm for in vitro fertilization, as described by Gordon et al. (1983) Methods Enzymol. 101:411–432 although any suitable method of making transgenic animals is acceptable. Briefly, the 10–14 week old females are superovulated by intraperitoneal injection of 5 I.U. of pregnant mare's serum followed 48 hours later by 2.5 I.U. of human chorionic gonadotropin. These mice are then sacrificed and the eggs removed. The 10–14 week old males are also sacrificed and the mature sperm harvested from the vas deferens and caudal epididymis. The eggs and sperm are frozen prior to in vitro fertilization. To increase fertilization, zona drilling of each egg is performed using micropuncture techniques. Following in vitro fertilization, the zygotes with prominent pronuclei are selected and loaded into culture dishes containing microdrops of culture medium under mineral oil. Next, the embryos are placed on the stage of a phase contrast microscope and, while being held in place by a suction needle, the human ALA-D genomic DNA is microinjected until swelling of the pronuclei is noticeable.

After microinjection of about 100–200 copies of one of the ALA-D alleles, the embryos are returned to the incubator and examined after 1 hour. Survivors are selected and implanted into the oviducts of pseudopregnant females obtained by mating with vasectomized males. After the pups are born, tail clips are used as a source of DNA for Southern hybridization (or PCR amplification) with a unique portion of the first human ALA-D intron which has no homology with the mouse intron. Positive animals are used for breeding. Second generation animals carrying the human ALA-D allele must carry the gene in the germ line.

EXAMPLE 1

Screening for ALA-D polymorohisms

In order to screen for the ALA-D restriction fragment length polymorphisms (RFLP), an 1170 base pair (bp) cDNA isolated from an adult liver cDNA library according to the method described by Wetmur et al., "Human Delta-aminolevulinate Dehydratase: Nucleotide Sequence of a Full-length cDNA Clone", Proc. Natl. Acad. Sci. USA, 83:7703–7707 (1986), was used as a probe for restriction endonuclease analysis of human lymphoblastoid cell genomic DNA isolated as described in Sambrook et al. (1989) and analyzed using the electrophoresis, transfer and hybridization methods of Southern, "Detection of Specific Sequences Among DNA Fragments Separated by Gel Electrophoresis", J. Mol. Biol., 98:503–517 (1975). DNA was obtained from over 30 unrelated individuals, digested with more than 20 restriction endonucleases and fragments greater than 1 kb were analyzed by Southern blot analysis.

No polymorphism was detected by Southern blot hybridization using a battery of restriction endonucleases with six base recognition sequences. One polymorphism was detected using restriction endonucleases with four base recognition sequences. With RsaI, the presence or absence of the polymorphic site resulted in 2.2 or 3.0 kb fragments respectively.

Based on the distribution of Rsa I sites in the ALA-D gene, the RsaI polymorphism was located in Exon 4 (the third coding exon in Table 3), 3.4 kb 5' of the polyadenylation signal and 2.0 kb 3' of the initiation codon. The polymorphism is a single base pair change from T to C at nucleotide 168 of the cDNA coding sequence. This transition does not affect the amino acid sequence of ALA-D).

EXAMPLE 2

Cloning the ALA-$D^2$ gene

In order to clone the ALA-$D^2$ gene a cDNA sequence encoding ALA-$D^2$ was obtained by the following method. RNA was extracted from lymphoblastoid cells of an individual who had been shown to be homozygous for the ALA-$D^2$ allele by starch gel electrophoresis. The method of Chirgwin et al., (1979) "Isolation of Biologically Active Ribonucleic Acid From Sources Enriched in Ribonuclease", Biochem., 18:5294–5299 was used with the following modifications: the guanidinium thiocyanate solution contained 25 mM sodium thiocyanate and 0.03% instead of 0.1% Antifoam A; the CsCl solution contained 0.02% instead of 0.2% diethylpyrocarbonate. CDNA synthesis was carried out using the cDNA Synthesis System of BRL, Inc. according to the manufacturer's instructions. Briefly, 10 mg of total RNA was reverse transcribed into cDNA using oligo-dT as the primer. All oligodeoxynucleotides were synthesized on an Applied Biosystems Model 380B oligonucleotide synthesizer using standard phosphoramidite chemistry according to the manufacturer's instructions. ALA-D-specific primers for the 5' and 3' untranslated regions of the gene

SEQ ID NO: 5  5'AGAGGCGAATTCCCAATGCCCCAGGAGCCC3' and

SEQ ID NO: 6  5'GTTCTAAAGCTTGGGCCTGGCACTGTCTCC3' respectively) were synthesized to include 5' EcoRI or HindIII sites, respectively. Amplification of ALA-D cDNA was carried out using the polymerase chain reaction (PCR) according to the method of Saiki et al. (1988) "Primer-directed Enzymatic Amplification of DNA With a Thermostable DNA Polymerase", Science, 239:487–491. Ten to 12.5 µl of first strand mixture, without prior precipitation, was mixed with ALA-D-specific primers. The cDNA-RNA hybrid was denatured by heating at 100° C. for 5 minutes, then quenching on ice for 5 minutes. 45 cycles of amplification were executed using denaturation at 94° C. for 1 minute, annealing at 53° C. for 1 minute and extension at 72° C. for 3 minutes with the final cycle extended to 10 minutes. PCR was performed using either the GeneAmp DNA Amplification Reagent Kit according to the manufacturer's instructions (Perkin-Elmer Cetus) or using Taq DNA Polymerase according to the manufacturer's instructions (Promega) with 1.0 to 2.2 µM primers and 20 µg/ml genomic DNA or 4 ng/ml plasmid DNA template.

Following the appropriate methods of Sambrook et al. (1989), the cDNA PCR product was extracted once with phenol:chloroform:isoamyl alcohol (25:24:1), twice with chloroform:isoamyl alcohol (24:1), ethanol precipitated, and digested with EcoRI and HindIII. The digest was heated to 65° C. for 20 minutes, ethanol precipitated, redissolved, ligated into EcoRI and HindIII digested pUC19 (25 µg/ml) and transformed into E. coli DHS using the protocol of Kushner, "Genetic Engineering", Boyer, Nicosia, eds. Elsevier/North-Holland Biomedical Press, Amsterdam, pp. 17–23 (1978) without dimethylsulfoxide. Colonies not expressing β-galactosidase were propagated, and plasmid DNAs were prepared. T4 DNA ligase, T4 polynucleotide kinase and all restriction endonucleases were purchased from New England Biolabs, Inc. or Promega, Inc. and used according to the manufacturer's instructions.

Double-stranded DNA sequencing of supercoiled plasmid templates was performed according to the instructions in the Sequenase DNA Sequencing Kit of United States Biochemical Corporation, Inc., at least 2 µg of DNA was used in each reaction. The cDNA sequence obtained is presented in Table 2.

The ALA-D$^2$ cDNA sequence obtained showed that a single base pair change of a G to C at position 177 compared to the ALA-D$^1$ sequence. Wetmur et al. (1986). The transversion results in a change of amino acid 59 from positively charged lysine to neutral asparagine and in the creation of an MspI (CCGG) restriction endonuclease site. In the genomic DNA, the MspI polymorphism is located in exon 4 (the third coding exon in Table 3), only 9 base pairs away from the RsaI polymorphic site described in Example 1 As a result, the same PCR method as described in example 3 can be used to amplify DNA for the determination of the RsaI polymorphism and the presence or absence of the MspI restriction endonuclease site.

The only nucleotide sequence difference found between the sequences of the ALA-D$^1$ and ALA-D$^2$ alleles corresponds to a change in one predicted amino acid from a positive lysine to a neutral asparagine, which accounts for the difference in the electrophoretic mobilities of the ALA-D 1-1, ALA-D 1-2 and ALA-D 2-2 charge isozymes.

EXAMPLE 3

Correlation of ALA-D genotype and ALA-D charge isozyme phenotype

In order to correlate ALA-D genotype and charge isozyme phenotype, aliquots of residual blood collected with informed consent from patients &&&KEPundergoing Tay-Sachs screening at Mount Sinai and Beth Israel Hospitals in New York City were used for either gel electrophoresis or PCR analysis, or both. Blood samples for analysis by electrophoresis were centrifuged at 1600 rpm in a Sorvall RT6000 for 30 minutes and the plasma and buffy coat were removed. The remaining red blood cells were mixed several times by inverting with one half volume of saline and centrifuged at 1600 rpm for 10 minutes. This erythrocyte washing procedure was repeated. A 0.5 ml sample of packed erythrocytes was mixed with an equal volume of lysis buffer (1 mM KH$_2$PO$_4$+KOH, pH 6.8, 1 mM MgCl$_2$, 1 mM dithiothreitol (DTT) and 0.05% Triton X-100) and centrifuged for 1 minute at 12,000 rpm in a Fisher Model 235C microcentrifuge. Lysed red blood cell samples were frozen until used.

The ALA-D isozyme phenotypes were determined following cellulose acetate gel electrophoresis (Cellogel). Lysates (7.5 ml) were diluted into 0.01M phosphate buffer, applied to the gel and separated by electrophoresis for 2 hr at 200 V at 4° C. in 0.1M sodium phosphate, pH 6.8. The cellogel was first incubated in PBS with rabbit polyclonal anti-human ALA-D antibody directed at human ALA-D purified by the method of Anderson and Desnick, "Purification and Properties of delta-aminolevulinate Dehydratase from Human Erythrocytes", J. Biol. Chem., 254:6924–6930 (1979), then with biotinylated goat anti-rabbit IgG and finally with a preformed avidin and biotinylated horseradish peroxidase complex as described in the Vectastain ABC kit (Vector Laboratories).

In order to determine the ALA-D genotype, samples for PCR analysis were prepared by the whole blood protocol as described by Perkin-Elmer, Cetus. Oligodeoxynucleotides were synthesized 5' and 3' to the exon with the ALA-D polymorphisms. The 5' and 3' oligodeoxynucleotide sequences were

SEQ ID NO: 1    5'AGACAGACATTAGCTCAGTA3' and

SEQ ID NO: 2    5'GGCAAAGACCACGTCCATTC3' respectively. The amplification program was the same as described in Example 2 except the annealing temperature was 55° C.

PCR products were cleaved with RsaI and/or MspI and analyzed by fluorography following agarose gel electrophoresis with ethidium bromide. The 916 bp PCR product was unaffected by RsaI digestion if the allele was RsaI, but was cleaved into 523 and 393 bp fragments if the allele was RsaI$^+$. The Bluescript SK (Stratagene, Inc.) vector, which contains two RsaI cleavage sites, was added to RsaI-only digestion reactions as a control for incomplete digestion.

All blood samples that were determined to be either ALA-D 1-2 or ALA-D 2-2 and eighty seven blood samples that were determined to be ALA-D 1-1 by cellulose acetate gel analysis were further analyzed for ALA-D$^1$ and ALA-D$^2$ alleles by MspI cleavage of the PCR products. The 916 bp PCR product was cleaved by MspI digestion into a 582 bp fragment if the allele was ALA-D$^1$ and into a 511 bp fragment if the allele was ALA-D$^2$. The products were analyzed by agarose gel electrophoresis. In all cases of ALA-D 1-2 individuals the expected heterozygote agarose gel pattern was observed. Likewise, MspI cleavage of PCR products from all samples with the ALA-D 2-2 phenotype resulted in a single 511 bp band. Haplotype assignments of RsaI and MspI heterozygotes were made by double-digestion.

Analysis of a random population of 428 normal Caucasian individuals revealed that the ALAD$^1$(MspI$^-$) and ALAD$^2$ (MspI$^+$) allele frequencies were 0.88 and 0.12, respectively. The allele frequencies for the RsaI$^-$ and RsaI$^+$ alleles in the same population were 0.75 and 0.25, respectively. Individually, the MspI and RsaI RFLPs were in Hardy-Weinberg equilibrium ($\chi^2$ MspI=3.5, df=2, p>0.10; $\chi^2$ RsaI= 1.88, df=2, p>0.25). Based on the above frequencies, the expected MspI/RsaI haplotypes would be ALAD[1] (MspI−)/RsaI+, 0.66; ALAD[1]/RsaI+, 0.22; ALAD[2]/RsaI−, 0.09 and ALAD[2]/RsaI+, 0.03. However, the two RFLPs were in linkage disequilibrium ($\chi^2$=22, df=1, p<0.001). Of the 259 ALAD[1] alleles studied, 27.4% were RsaI+, whereas only 5% of 101 ALAD[2] alleles were RsaI+. The expected number of ALAD[1]/RsaI+ and ALAD[2]/RsaI+ were each 25%, thus the ALAD[2]/RsaI+ allele was highly underrepresented.

The polymorphism information content (PIC) for these haplotypes is 0.45, a reasonably informative (0.5>PIC>0.25) value. Botstein et al., (1980) "Construction and Genetic Linkage Map in Man Using Restriction Fragment Length Polymorphism", Am. J. Hum. Genet., 32:314–31.

Of the samples where ALA-D electrophoretic phenotypes were determined by Cellogel electrophoresis and MspI genotypes all were determined by RFLP analysis, all phenotypes correlated with genotypes. In another unrelated study, one individual was identified by starch gel electrophoresis as having the ALA-D 2-2 isozyme phenotype, but genotype analysis revealed that this individual had one ALA-D[2] allele and one ALA-D[1] allele. Thus, there may be another (other) rare mutation(s) which lead to the same charge isozyme phenotype or, alternatively, this ALA-D[1] allele which does not have the MspI site may not have been expressed. Nevertheless, the observed nucleotide substitution results in both the MspI RFLP and the polymorphic ALA-D charge isozymes in the vast majority of individuals.

We claim:

1. A recombinant DNA vector into which some or all of a DNA sequence encoding ALA-$D^2$ has been cloned.

2. The recombinant DNA vector according to claim 1 wherein the DNA sequence encoding ALA-$D^2$ comprises an oliogodeoxyribonucleotide having the sequence

SEQ ID NO: 3

| Sequence | Position |
|---|---|
| GAGACCGGAG CGGGAGACAG CGGTGACAGG AGCAGCGGCC GGGAGCCCTT | 50 |
| AGGGAGGCAG ACAGAGCCTG CAGCCAATGC CCCAGGAGCC CTCGGTTCCA | 100 |
| ACCAACTGAT GCCCTGTGC CCACTGGCCC ACGCC ATG CAG CCC CAG | 147 |
| TCC GTT CTG CAC AGC GGC TAC TTC CAC CCA CTA CTT CGG GCC | 189 |
| TGG CAG ACA GCC ACC ACC ACC CTC AAT GCC TCC AAC CTC ATC | 231 |
| TAC CCC ATC TTT GTC ACG GAT GTT CCT GAT GAC ATA CAG CCT | 273 |
| ATC ACC AGC CTC CCA GGA GTG GCC AGG TAT GGT GTG AAC CGG | 315 |
| CTG GAA GAG ATG CTG AGG CCC TTG GTG GAA GAG GGC CTA CGC | 357 |
| TGT GTC TTG ATC TTT GGC GTC CCC AGC AGA GTT CCC AAG GAC | 399 |
| GAG CGG GGT TCC GCA GCT GAC TCC GAG GAG TCC CCA GCT ATT | 441 |
| GAG GCA ATC CAT CTG TTG AGG AAG ACC TTC CCC AAC CTC CTG | 463 |
| GTG GCC TGT GAT GTC TGC CTG TGT CCC TAC ACC TCC CAT GGT | 525 |
| CAC TGC GGG CTC CTG AGT GAA AAC GGA GCA TTC CGG GCT GAG | 567 |
| GAG AGC CGC CAG CGG CTG GCT GAG GTG GCA TTG GCG TAT GCC | 609 |
| AAG GCA GGA TGT CAG GTG GTA GCC CCG TCG GAC ATG ATG GAT | 651 |
| GGA CGC GTG GAA GCC ATC AAA GAG GCC CTG ATG GCA CAT GGA | 693 |
| CTT GGC AAC AGG GTA TCG GTG ATG AGC TAC AGT GCC AAA TTT | 735 |
| GCT TCC TGT TTC TAT GGC CCT TTC CGG GAT GCA GCT AAG TCA | 777 |
| AGC CCA GCT TTT GGG GAC CGC CGC TGC TAC CAG CTG CCC CCT | 819 |
| GGA GCA CGA GGC CTG GCT CTC CGA GCT GTG GAC CGG GAT GTA | 861 |
| CGG GAA GGA GCT GAC ATG CTC ATG GTG AAG CCG GGA ATG CCC | 813 |
| TAC CTG GAC ATC GTG CGG GAG GTA AAG GAC AAG CAC CCT GAC | 945 |
| CTC CCT CTC GCC GTG TAC CAC GTC TCT GGA GAG TTT GCC ATG | 987 |
| CTG TGG CAT GGA GCC CAG GCC GGG GCA TTT GAT CTC AAG GCT | 1029 |
| GCC GTA CTG GAG GCC ATG ACT GCC TTC CGC AGA GGT GCT | 1071 |
| GAC ATC ATC ATC ACC TAC TAC ACA CCG CAG CTG CTG CAG TGG | 1113 |
| CTG AAG GAG GAA TGA TGGAGACAGT GCCAGGCCCA AGAACTAGAA | 1158 |
| CTTTAAAACG TTCCCGGGGC CTCAGACAAG TGAAAACCAA AGTAAATGCT | 1208 |
| GCTTTTAGAA CTGT | 1222 |

3. The recombinant DNA vector according to claim 1, wherein the vector is selected from the group consisting of plasmids, viruses, and retroviruses.

4. An in vitro cellular system transformed with the recombinant vector of claim 1.

5. The cellular system according to claim 4, wherein the system is selected from the group consisting of mammalian cell lines, yeast, bacteria and insect cell lines.

6. A recombinant DNA vector comprised of oliogodeoxyribonucleotide having the sequence

SEQ ID NO: 4

| | |
|---|---|
| -600 | gagaccatcc tgggaagcat ggcaagacct ccatctctac aaaaaattcg |
| -550 | aaaattagct ggatgttgtg gtgcacacct gcagtdccag ctacttggga |
| -500 | ggctgagttg ggagaaacag ttgagcccgg gaggtcaagg ctgcagtgag |
| -450 | tcgagattgc accactgcac tccagcctgg gcgacagaga ccctgtgtga |
| -400 | aaaaaaaaaa aagaagagaa ttttttttaa acagtcattg cttgctcaga |
| -350 | tgtttacttt aaaagataat aatgaacaag aagcagtcac ataaaataca |
| -300 | agcccaaatt ttatatcatt agattctgat tgtcatgaaagtttctaaag |
| -250 | acttactttc atttctcaac ttaccttgtt gaccagcagg gattggtgaa |
| -200 | ccaggctgtg agtagcattg ggctagagag aggggaggca ggaatctaga |
| -150 | agagctgttt tccagatgtg accatctcct gaggacaggg accatgtcct |
| -100 | atgtgccacc catcaccccc cacagACAGA GCCTGCAGCC AATGCCCCAG |
| -50 | GAGCCCTCGG TTCCAACCAA CTGATGCCCC TGTGCCCACT GGCCCACGCC |
| 1 | ATGCAGCCCC AGTCCGTTCT GCACAGCGGC TACTTCCACC CACTACTTCG |
| 51 | GGCCTGGCAG ACAGCCACCA CCACCCTCAA TGCCTCCAAC CTCATCTACC |
| 101 | CCATCTTTGT CACgtgagtc tccaagaatg ggccaggcct ctgctctgct |

SEQ ID NO: 4

```
 151  ggttggggtt ggggttgggg agggagtgtt gactggagcg ggcatcagta
 201  tggctggggg tggcaaagtg agctgtcagc ttgaaattca aggcactgga
 251  agcaggctac ttggattaag gacaggaatc ttaggaacaa aacaaacttt
 301  gaaagaactc attcatccca tttggaaaat tagaagaata acccttgcct
 351  gccatcctga gctcttgcag taagacagaa gctgagaagg tgctctgtac
 401  attgtaaagt gctatgtacc tgtaagagat ggcagtcatt gaggctgggc
 451  acggtggctc acgcctgtaa tcccagcact ttgggaggct gaggcaggcg
 501  gatcacgagg tcaggagatc gagaccatcc tggctaatat ggtgaaaccc
 551  tgtctctact aaaaacacaa agaaattagc caggcgtggt ggcgggtgcc
 601  tgtagtccca gctacttggg aggctgaggc aggagaatgg cgtgaacccg
 651  ggaggcggag cttgcagtga gccgagattg caccacttca ctccagcctg
 701  ggcgacagag ccagactcca tctcaaaaaa aaaaaaaaaa aaaagagatg
 751  gcaatcgtga ttgttaataa taatgcagac atttactgag tacttactat
 801  ctaccaggta ctatgctaag cacctacaca cattatctca ttcaattctg
 851  agagcatttg tatgaagaag gagtagctat cctctagaac atcagctcca
 901  tgagggcagg gatgtttgtc tattttgttc actgttgtat catcagggcc
 951  tagaacagta cttggcacat aataagtact caataaatat ttgttgaatg
1001  aatgaattaa ccacgcatga tatagatgaa ggcctaaggc tcaaagagat
1051  gatagaactt ggccacggtc acccaggcag taagtggctg ggatagaaag
1101  caaggacctg ccaaattcag agtccaagtt cttaaccact taattccttc
1151  ctgtaattac cgttcttta gtacagttgc tagtgttgtc actgttattc
1201  ttgttgttcc tattattatt tcaggccctg ggcttggcca ggcagggaag
1251  ccagacactg gatcccatcc tcctcccacc atctccactt ccatatttct
1301  ttcctgcttc ccaaccatcc ctctcagtcg cccccgcacc actggcccctt
1351  cccacagcta ccaatccata tcccaccccc gctcttgcag GGATGTTCCT
1401  GATGACATAC AGCCTATCAC CAGCCTCCCA GGAGTGGCCA Ggtaggagac
1451  gtggagttgg ggggccagcg ggtggtggag ggagagattc cacaggtgga
1501  agtgctggga ggcagaagca gacctaggaa gtagaagatg cggacagaca
1551  gacattagct cagtagagga aagggtttcc ccggggccag agctgttcca
1601  cagtggaagg ggcagcccca taaagtaaag agctacccat cacccgagac
1651  gtcgtggcag aggctgttgc agaagggagc tgaactgcag atgggagttc
1701  aaaaagaggg cctcgaagga gccttccaca gccgaattcc ggagctctgc
1751  tactcagggc ctcagtcttc cctcctatt agtggatgca tccctgcccc
1801  ttctgtcctg ggggcttgag ccctcctggt gccatatgca gcttggtttc
1851  taacagaggc acacagtgtg gtggggtccg gaggaccgtt gcctgggacc
1901  tgccttcctt caaccccctct acccacaccc acacagGTAC GGTGTGAACC
1951  GGCTGGAAGA GATGCTGAGG CCCTTGGTGG AAGAGGGCCT ACGCTGTGTC
2001  TTGATCTTTG GCGTCCCCAG CAGAGTTCCC AAGgtgaaga atcaaaggaa
2051  gggctaagaa gggaggttgc ctcacgcccg taatcccagc acttttggag
2101  gccaaagtgg gtggatcact tgagcccagg attttgagac cagcctggac
2151  aacatggcaa aacccatctc tacaaaaaat acaaaagtta gctgggtgtg
2201  ggggtatgtg cctgtagtcc cagctactcg ggaggtggag aggtgggagg
2251  attgcttgag cccagaaagt cgaggctgca gtgagccaaa atcgcgccag
2301  tgcactctag cctgggtgac agagcaagac cctgtctcca atacaaacag
2351  aaaaaggaag ggaggttggg caaaggtgga ctgagggtcc acactgactg
2401  caccctcact cccacattgt gctggccctg gggccacagg tgaatggacg
2451  tggtctttgc ccttaagtca gcacccatgt agggtcggtc ctctgtgctt
2501  ccttatccag gggctgtgat gatgaaggaa ggagaaggcc.agggctatgc
2551  tctgtgatgg ctgtcatcct gccttccaaa gctacatgta atagacacac
2601  tgctttgtcc ctcccctgcc cctagGACGA GCGGGGTTCC GCAGCTGACT
2651  CCGAGGAGTC CCCAGCTATT GAGGCAATCC ATCTGTTGAG GAAGACCTTC
2701  CCCAACCTCC TGGTGGCCTG TGATGTCTGC CTGTGTCCCT ACACCTCCCA
2751  TGGTCACTGC Ggtgagttcc ctccctccca ccagccctgc tgccacccac
2801  actcctactg cccacttctc aacagggtgg ggacagccag ggcccaaggt
2851  gctccccaaa acccagtcat ctgtcctgaa gGGCTCCTGA GTGAAAACGG
2901  AGCATTCCGG GCTGAGGAGA GCCGCCAGCG GCTGGCTGAG GTGGCATTGG
2951  CGTATGCCAA GGCAGgtgag tgaaccacca gcagggatgg gcacctctgg
3000  gtcaggaggt ggcagagtgg ctaggagggc cccagagttc tgaaggccac
3051  cctctgcccc ccagGATGTC AGGTGGTAGC CCCGTCGGAC ATGATGGATG
3101  GACGCGTGGA AGCCATCAAA GAGGCCCTGA TGGCACATGG ACTTGGCAAC
3151  AGGgtaaggg cagggaatgc agcacagggc tggcaggaga tagtctgcac
3201  cagccctgcc cccgtgtctg ctaagaatca cagaactgcc gggcgtgttg
3251  gctcacacct gtagtcccag cactttggga ggctgaggca ggtagatcac
3301  ttgaggtcag gggttcaaga ccagcctggc caacatggtg aaaccccatc
3351  tctactaaaa acacaaaaat tagctgggcg tggtggcagg cgcctgcaat
3401  cccagctact ggggaggctg aggcaggaga atcgcttgaa cccacgaggc
3451  agtgagctga gatcatgcca ctgcacttca gcctggatga cagagctaga
3501  ctccatctca aaaaaaaaaa gaatcacaga actgaagaca gtgctggatg
3551  aggctttggg gaaccattta aacctctggg cctctgcagg gaaatcaagc
3601  ccagcactcc aacaggacca gaacacaggc agtctccttc ccagcctagg
3651  ttctttctct ccctgccaca tcaccctggg atacctggca agggccgaat
3701  aagccaagac ctccattgtc tccccatagG TATCGGTGAT GAGCTACAGT
3751  GCCAAATTTG CTTCCTGTTT CTATGGCCCT TTCCGgtgag caggggtggg
3801  caggggtctg ctgtgaatcc ctgccctttg gcccaaagct ggagcccacc
3851  ctgatgactc tgctttgcag GGATGCAGCT AAGTCAAGCC CAGCTTTTGG
3901  GGACCGCCGC TGCTACCAGC TGCCCCCTGG AGCACGAGGC CTGGCTCTCC
3951  GAGCTGTGgt gagtgactag gacttgagcc ccacctcag cccctccta
4001  ggcaccaccc acattatacc ctcatccctt agGACCGGGA TGTACGGGAA
```

SEQ ID NO: 4

```
4051  GGAGCTGACA TGCTCATGGT GAAGCCGGGA ATGCCCTACC TGGACATCGT
4101  GCGGGAGGTA AAGGACAAGg tgagcacagg tacgaggcaa aggggctca
4151  gggggctggg acagagtttt ccacagactc tggaatctca gagttggaag
4201  cagtttgccc ttaagcatgc atcctctcct ccccttccct gcccaggaac
4251  catcgtggcc ttctatgtcg gggcttgcac gagcctcaaa cagccctgct
4301  ttaacagttc aagagtgggc caggctgcca gccgcagtaa cccaggacac
4351  ggggctcaag atggtcacag attgagcagg ggggaaggga cgcttccaga
4401  gccacatcca ccctccattt cagcctgtct ccctgtctgc ttccctgcag
4451  CACCCTGACC TCCCTCTCGC CGTGTACCAC GTCTCTGGAG AGTTTGCCAT
4501  GCTGTGGCAT GGAGCCCAGG CCGGGGCATT TGATCTCAAG GCTGCCGTAC
4551  TGGAGGCCAT GACTGCCTTC CGCAGAGCAG gtaggcaggc aagggtgggg
4601  tgttttgacc tgcgccacag ggactgataa gcactctgcc tagatcgggg
4651  aacgacgtcc tgagagcttg ggatcttatt ccgggaatta ctagtgatct
4701  aaacagacac acactgagga agagatatgg aactgcagca tagaacacgg
4751  cccggtgaag caagcagagc ccttcattt tggttgtgag aacgtggcaa
4801  gccacttctc tgaacctcag tgtcctcacc cataactggataactgggga
4851  taagatacct ggtgcgtggt tgtcctgagg attaaatgaa gtaatatcac
4901  tccataaagg ggactcattt tgttagaatt gcacaccagc atgggaagga
4951  acttgcctct tatatttcct tcactgtgca ttttattctt tggtaaactg
5001  aggcccccaaa agaggaaatg acttgcccaa gaaatagagt ttcccaaagc
5051  tgggctccgt ctcatgtggt gtgcccacag gctgtgcttc ttcatggtag
5101  ccttcttccc cgcctggcct tcccatcgca gaaggtgtgc tcagagctga
5151  tcagcgtccc cccagcaact ttctgcatct ctcccaacac agGTGCTGAC
5201  ATCATCATCA CCTACTACAC ACCGCAGCTG CTGCAGTGGC TGAAGGAGGA
5251  ATGATGGAGA CAGTGCCAGG CCCAAGAACT AGAACTTTAA AA>TCCCG
5301  GGGCCTCAGA CAAGTGAAAA CCAAAGTAAA TGCTGCTTTT AGAACTGTgc
5351  cctcatgccc tcttcctgct cacatgctag cggggcccag cagccctggg
5401  tggttttgcc agcatgctaa ctcttgtaac tcgcagctgc atcctatgag
5451  ctctcccaag ctt
```

7. The recombinant DNA vector according to claim 6, wherein the vector is selected from the group consisting of plasmids, viruses, and retroviruses.

8. An in vitro cellular system transformed with the recombinant DNA vector of claim 6.

9. The cellular system according to claim 8, wherein the system is selected from the group consisting of mammalian cell lines, yeast, bacteria and insect cell lines.

* * * * *

UNITED STATES PATENT AND TRADEMARK OFFICE
CERTIFICATE OF CORRECTION

PATENT NO. : 5,840,578

DATED : November 24, 1998

INVENTOR(S) : Desnick et al.

It is certified that error appears in the above-identified patent and that said Letters Patent is hereby corrected as shown below:

IN THE PATENT
ON THE COVER
[56] References Cited, OTHER PUBLICATIONS
Under Jordan et al.: "5-aminolaevulinate Deshydratase"
should read -- 5-aminolevulinate Dehydratase

[56] References Cited OTHER PUBLICATIONS
Under Petrucci et al.: "Delta-aminolaevulinate Deshydrase"
should read -- Delta-aminolevulinate Dehydratase

[56] References Cited, OTHER PUBLICATIONS
Under Battistuzzi et al.: "δ-aminolaevulinate Deshydrase"
should read -- δ-aminolevulinate Dehydratase

[56] References Cited, OTHER PUBLICATIONS
Under Potluri et al.: "δ-aminolaevulinate Deshydratase"
should read -- δ-aminolevulinate Dehydratase --

[56] References Cited, OTHER PUBLICATIONS
Under Ben-Ezzer et al.: "Dehydrase" should read
-- Dehydratase --

[56] References Cited, OTHER PUBLICATIONS
Under "Connor" et al.: "Connor" should read -- Conner --

UNITED STATES PATENT AND TRADEMARK OFFICE
CERTIFICATE OF CORRECTION

PATENT NO. : 5,840,578
DATED : November 24, 1998
INVENTOR(S) : Desnick et al.

It is certified that error appears in the above-identified patent and that said Letters Patent is hereby corrected as shown below:

[56] References Cited, OTHER PUBLICATIONS
Under Wetmur et al.: "Deshydratase" should read
-- Dehydratase --

[56] References Cited, OTHER PUBLICATIONS
Under Astrin et al.: "Deshydratase" should read
-- Dehydratase --

UNITED STATES PATENT AND TRADEMARK OFFICE
CERTIFICATE OF CORRECTION

PATENT NO. : 5,840,578
DATED : Nov. 24, 1998
INVENTOR(S) : Desnick et al.

It is certified that error appears in the above-identified patent and that said Letters Patent is hereby corrected as shown below:

Col. 4, Table 1: ">30" (both occurrences) should read
-- <30 --

Col. 4, Table 1: Inside the table, the _third_ row of numbers (beginning with "1278" -- first occurrence) should be moved up one line, so as to be associated with the _first two_ rows of numbers, as totals thereof.

Col. 4, Table 1: Inside the table, the _sixth_ row of numbers (beginning with "1278"-- second occurrence) should be moved up one line, so as to be associated with the _fourth and fifth_ rows of numbers, as totals thereof.

Col. 4, Table 1: Inside the table, the _ninth_ row of numbers (beginning with "345") should be moved up one line, so as to be associated with the _seventh and eighth_ rows of numbers, as totals thereof.

Col. 6, line 26: "sequences. For" should read -- sequences; for --

Col. 6, line 44: "mamalian" should read -- mammalian --

UNITED STATES PATENT AND TRADEMARK OFFICE
CERTIFICATE OF CORRECTION

PATENT NO. : 5,840,578
DATED : November 24, 1998
INVENTOR(S) : Desnick et al.

It is certified that error appears in the above-identified patent and that said Letters Patent is hereby corrected as shown below:

Col. 13, line 18: "DHS" should read --DH5--

Col. 13, line 41: "Example 1 As" should read --Example 1. As --

Col. 13, line 59: [Query: "&&&KEPundergoing" should read -- undergoing -- ?]

Signed and Sealed this

Fourteenth Day of March, 2000

Attest:

Q. TODD DICKINSON

*Attesting Officer*     Commissioner of Patents and Trademarks